US011525153B2

(12) United States Patent
Larimer et al.

(10) Patent No.: US 11,525,153 B2
(45) Date of Patent: Dec. 13, 2022

(54) METHODS AND SYSTEMS OF CHARACTERIZING AND COUNTING MICROBIOLOGICAL COLONIES

(71) Applicant: BATTELLE MEMORIAL INSTITUTE, Richland, WA (US)

(72) Inventors: Curtis J. Larimer, Richland, WA (US); Raymond S. Addleman, Benton City, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 1123 days.

(21) Appl. No.: 16/039,681

(22) Filed: Jul. 19, 2018

(65) Prior Publication Data

US 2020/0024634 A1 Jan. 23, 2020

(51) Int. Cl.

| | |
|---|---|
| ***C12Q 1/06*** | (2006.01) |
| ***G01N 21/45*** | (2006.01) |
| *C12M 1/34* | (2006.01) |
| *C12M 1/32* | (2006.01) |
| *C12M 1/00* | (2006.01) |
| *G01B 9/02055* | (2022.01) |

(52) U.S. Cl.

CPC ............... *C12Q 1/06* (2013.01); *G01N 21/45* (2013.01); *C12M 1/34* (2013.01); *C12M 23/12* (2013.01); *C12M 23/22* (2013.01); *G01B 9/02055* (2013.01)

(58) Field of Classification Search

CPC ........... C12Q 1/06; G01N 21/45; C12M 1/34; C12M 23/12; C12M 23/22; G01B 9/02055; G01B 11/2441; G06T 2207/10056; G06T 2207/30072; G06T 2207/30242; G06T 7/62

See application file for complete search history.

(56) References Cited

U.S. PATENT DOCUMENTS

2003/0082516 A1* 5/2003 Straus .............. G01N 33/56938 435/287.1

2010/0284016 A1* 11/2010 Teitell .................... G02B 5/126 359/398

(Continued)

FOREIGN PATENT DOCUMENTS

EP 2184346 A2 5/2010

OTHER PUBLICATIONS

Drazek, L., et al., Three-dimensional characterization of bacterial microcolonies on solid agar-based culture media, Journal of Microbiological Methods, 109, 2015, 149-156.

(Continued)

*Primary Examiner* — Michael P LaPage

(74) *Attorney, Agent, or Firm* — Kristen M. Clark

(57) ABSTRACT

Described herein are methods, systems, and non-transitory computer-readable media to non-destructively acquire three-dimensional profiles of cellular microbiological samples growing on the surface of a solid growth medium. Acquisitions can be performed by an optical microscope that includes a vertical scanning interferometer. The three-dimensional profiles can enable measurement of sample parameters of microcolonies, which can be made of microbial colony forming units. The methods and systems enable early and rapid detection and quantification of microbes.

18 Claims, 18 Drawing Sheets

(56) References Cited

U.S. PATENT DOCUMENTS

| | | | | |
|---|---|---|---|---|
| 2012/0277852 | A1* | 11/2012 | Shukla | A61L 26/0066 623/1.42 |
| 2014/0178865 | A1* | 6/2014 | Reed | G01N 33/57492 435/6.1 |
| 2016/0103118 | A1* | 4/2016 | Teitell | G01N 33/505 702/19 |
| 2016/0212989 | A1* | 7/2016 | Juodkazis | C12Q 1/24 |
| 2016/0272933 | A1 | 9/2016 | Larimer et al. | |
| 2021/0278393 | A1* | 9/2021 | Reed | A61K 45/00 |

OTHER PUBLICATIONS

Larimer, C., et al., Rapid nondestructive measurement of bacterial cultures with 3D interferometric imaging, Scientific Reports, 9, 1, 2019, 1-14.

Waters, M. S., et al., In search of the microbe/mineral interface: quantitative analysis of bacteria on metal surfaces using vertical scanning interferometry, Geobiology, 6, 2008, 254-262.

International Search Report/Written Opinion for International Application No. PCT/US2019/035781, International Filing Date Jun. 6, 2019, dated Sep. 30, 2019.

Zangle, T. A., et al., Quantification of Biomass and Cell Motion in Human Pluripotent Stem Cell Colonies, Biophysical Journal, 105, 2013, 593-601.

Zangle, T. A., Live-cell mass profiling: an emerging approach in quantitative biophysics, Nature Methods, 11, 12, 2104, 1221-1228.

* cited by examiner

1. SERIES OF IMAGES COLLECTED DURING VERTICAL SCAN

2. CORRELOGRAM COMPILED FOR EACH PIXEL IN FIELD OF VIEW

3. ENVELOPE FUNCTION TO DETERMINE MIDPOINT OF INTERFERENCE ENVELOPE FOR EACH PIXEL

4. CONVERSION OF ENVELOPE MIDPOINTS TO RELATIVE Z-HEIGHTS FOR EACH PIXEL

5. LEVELING AND SMOOTHING OF SURFACE PROFILE (REMOVE CURVATURE, SPHERICAL AND CYLINDRICAL FORM, PLANAR TILT, ETC.)

6. MASKING TO REMOVE NON-RELEVANT IMAGE AREAS

7. APPLICATION OF DATA FILLING ALGORITHM (INTERPOLATION WITH NEIGHBORING PIXELS USING MEAN, MAX, MIN OR OTHER VALUES)

8. FINE DETAIL SMOOTHING WITH GAUSSIAN REGRESSION FILTER, FOURIER FILTER, COMBINATIONS OF THESE, OR OTHERS WITH SETTINGS FOR HIGH PASS, BANDPASS, LOW PASS OR COMBINATIONS OF THESE

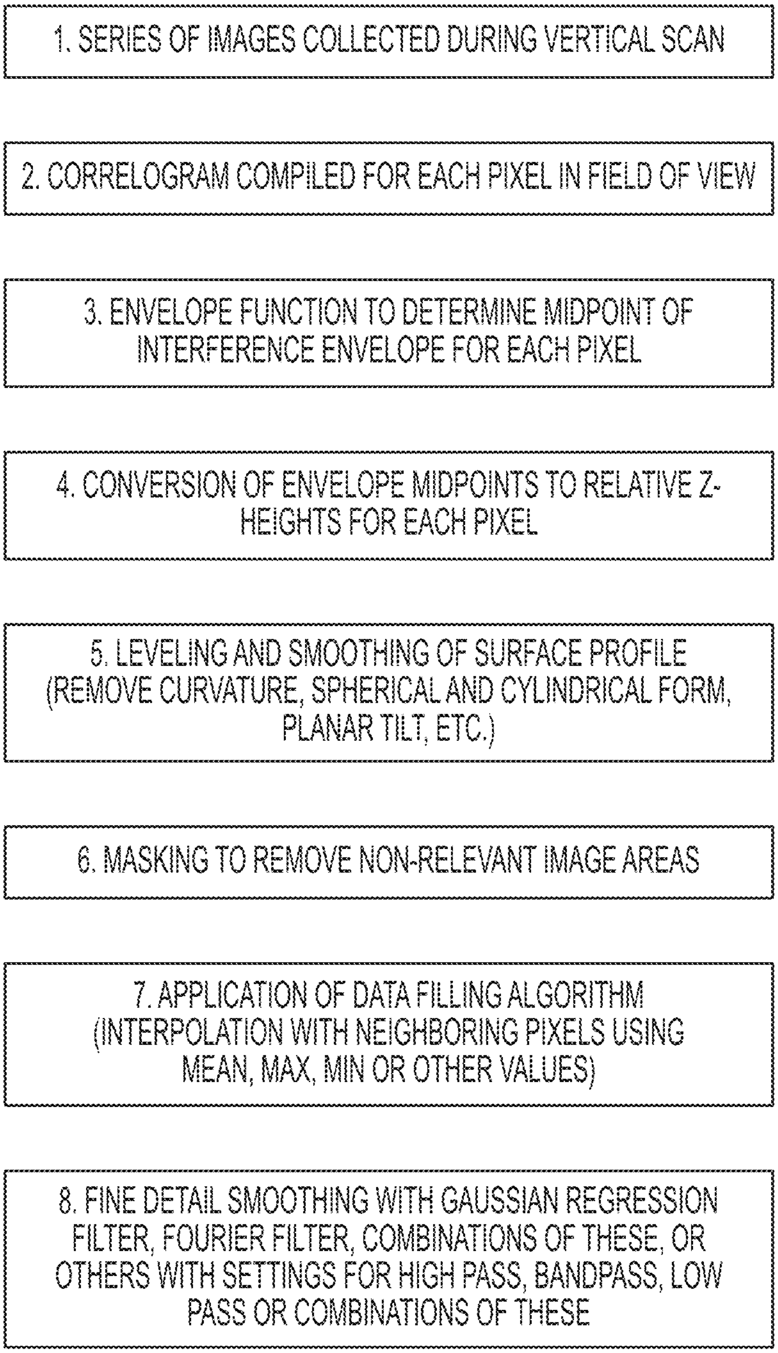

FIG. 17

1. SEARCH FOR REGIONS IN DATA SETS THAT HAVE PASSED THROUGH THE ROUTINE OF FIG 17 THAT HAVE PEAK VALUES OVER NEIGHBORING REGIONS THAT ARE GREATER THAN A THRESHOLD THAT IS A DEFINED MULTIPLE (OR FRACTION) OF THE SIZE OF A MICROBE OF INTEREST

2. FILTERING OF THE SET OF REGIONS FOUND IN (1) TO REMOVE REGIONS THAT ARE OUTLIERS ON A MEASURABLE DIMENSION OR PARAMETER (E.G., HEIGHT, AREA, VOLUME, MORPHOLOGY, ROUGHNESS, ETC.)

3. CALCULATION OF DIMENSIONS OR PARAMETERS FOR THE SET OF REGIONS OF INTEREST CREATED IN (2) INCLUDING THE TOTAL NUMBER OF REGIONS (COUNT), VOLUME OF ALL REGIONS, AVERAGE VOLUME OF REGIONS, HEIGHT OF REGIONS, AVERAGE HEIGHT OF REGIONS, ETC.

4. APPLICATION OF STEPS 1-3 ON MULTIPLE SETS OF DATA THAT WAS COLLECTED AS A SERIES OVER TIME (EACH OF WHICH HAS ALREADY PASSED THROUGH THE ANALYSIS ROUTINE OF FIG 17)

5. CALCULATION OF DATA SERIES PARAMETERS BASED ON TOTAL REGION VOLUME, AVERAGE REGION VOLUME, NUMBER OF REGIONS OF INTEREST AND OTHERS. PARAMETERS MAY BE GROWTH RATES, DOUBLING TIMES, RATES OF DECLINE, RATES OF INHIBITION, TIME-KILL CURVES, AND OTHER TIME-DEPENDENT PARAMETERS

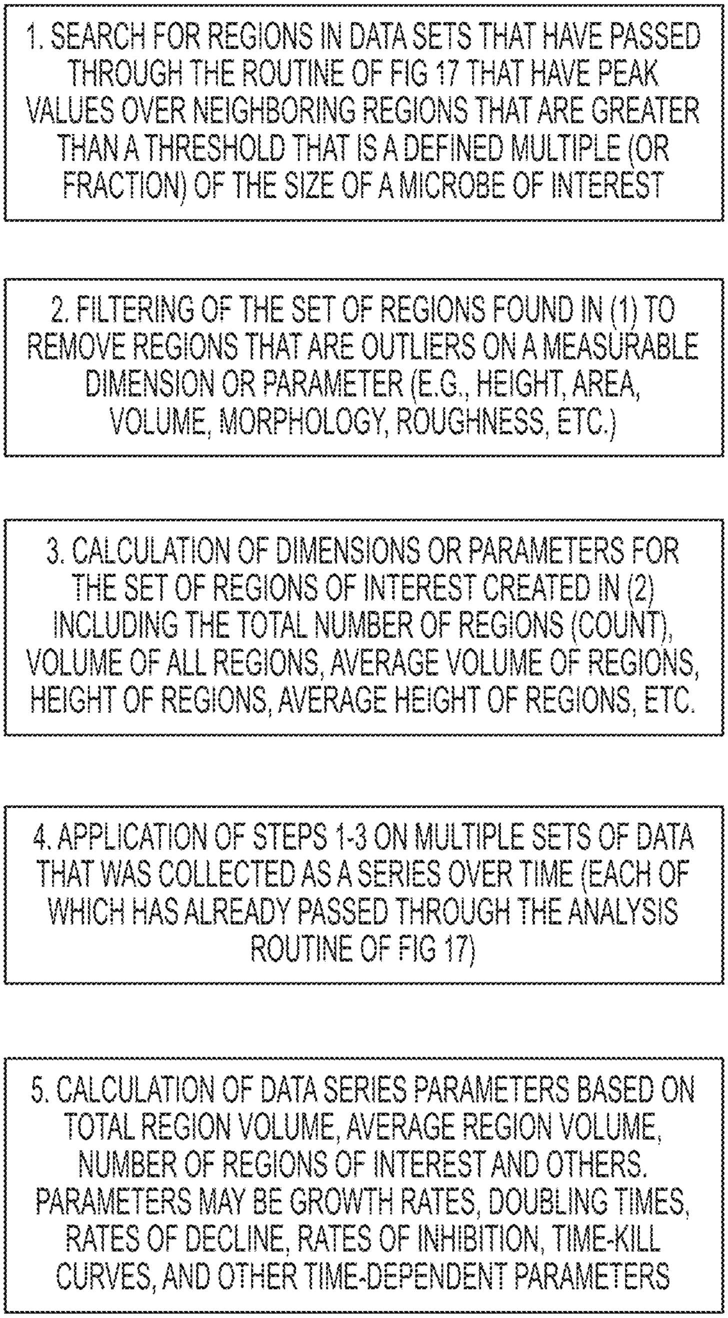

FIG. 18

METHODS AND SYSTEMS OF CHARACTERIZING AND COUNTING MICROBIOLOGICAL COLONIES

ACKNOWLEDGEMENT OF GOVERNMENT SUPPORT

This invention was made with Government support under Contract DE-AC0576RL01830 awarded by the U.S. Department of Energy. The Government has certain rights in the invention.

FIELD

The present disclosure relates generally to microbiological experiment techniques and more particularly to rapidly counting and/or characterizing microbiological colonies on a surface.

BACKGROUND

The agar plate as an example of a solid, microbiological growth medium has played an important role in bacteriology since the origins of the discipline. One of the most common means for qualitative and quantitative analysis of bacteria is the use of petri dishes that contain both growth nutrients and agar. The growth of a single bacterium in a defined location in the agar plate can give rise to a proliferating colony that is typically visible within one to three days but can easily extend to weeks depending on the species and growth conditions. In biomedical and food safety settings quantifying the colony forming units (CFU) on agar plates for a bacterial sample such as pathogenic *E. coli* can be informative for detecting and enumerating an infectious dose. Agar plates can also be selective and/or differential through the addition of specific nutrients, indicators, antibiotics, salts (e.g., Manitol for *S. aureus* detection), or other substrates (e.g., enzyme sensitive media to detect *E. coli*) and therefore also represent a powerful diagnostic tool for assessing antibiotic resistance or the presence of hallmark biochemical features indicative of a pathogenic organism. However, plating, inoculating, and waiting for microbes to develop colonies that are visible to the eye for counting is time-consuming. Microscopy may be used to see bacteria and small colonies sooner, but the magnification needed typically results in a narrow, often insufficient, field of view. There have been efforts to design computerized imaging systems and software that automate plate counting, however automation is not the rate limiting step and most systems do not utilize high-resolution 3D surface imaging. Accordingly, a need exists for systems, methods, and non-transitory computer readable storage medium storing computer-executable instructions that can in hours, not days, characterize and/or count microbiological colonies on solid growth media and/or provide high-resolution images of samples.

SUMMARY

Disclosed are methods, systems, and non-transitory computer readable storage media storing one or more programs comprising computer-executable instructions for rapidly counting and/or characterizing microbiological colonies on a surface. In some embodiments methods comprise non-destructively acquiring by a vertical scanning interferometer a three-dimensional (3D) profile that provides a height measurement of a microcolony on a surface. The microcolony can comprise a microbial colony forming unit (CFU). In certain embodiments, the surface comprises that of a solid growth medium. Alternatively, the surface can comprise a solid surface on which microbes grow. Examples include pipe or tube surfaces, prosthetic surfaces, device surfaces, furniture surfaces, and building structure surfaces. The surfaces can comprise polymers, metals, ceramics, glasses, and natural materials. In certain embodiments, the vertical resolution of the vertical scanning interferometer is less than or equal to 5 nm. In certain embodiments, said acquiring comprises laterally sampling an area of the growth medium that is greater than or equal to 10 mm, 8 mm, 5 mm, 3 mm, 1 mm, 0.5 mm or 0.05 mm across. A high vertical resolution is retained even while the lateral sampling area is large. In certain embodiments, lateral sampling occurs in a single image and is not a result of multiple stitched images. In certain embodiments, the vertical scanning interferometer is a white light interferometer. In certain embodiments, the method can further comprise computing a sample parameter based on the 3D profile with the height measurement. In certain embodiments, the sample parameter comprises a value based on microcolony height, aspect ratio, volume, number of microcolonies, microcolony morphology, or a combination thereof. In certain embodiments, methods can further comprise identifying species kind of the microbial CFU based on the sample parameter. In certain embodiments, methods can further comprise estimating a microbial CFU population value in a microcolony based on the sample parameter. In certain embodiments, said computing occurs at a non-zero time value that is less than 1 hour, 2 hours, 4 hours, 6 hours, or 8 hours after the microbial CFU is introduced to the solid growth medium. In certain embodiments, methods can further comprise tracking changes in the sample parameter over a period of time. In certain embodiments, methods can further comprise estimating a growth rate value of the microbial CFU based on the sample parameter and on changes over the period of time. In certain embodiments, methods can further comprise screening a plurality of samples by repeating said acquiring and said computing at each of a plurality of sample wells, each sample well comprising a solid growth medium. In certain embodiments, the plurality of sample wells have different solid growth media selected from the group comprising culture media, minimal media, selective media, differential media, transport media, and combinations thereof. In certain embodiments, the plurality of samples wells each have a non-zero dimension that is less than or equal to 50 mm, 30 mm, 15 mm, 10 mm, or 5 mm. In certain embodiments, methods can further comprise covering the surface of the solid growth medium with a lid comprising an optically transparent window through which a probe of the vertical scanning interferometer passes. The probe can be light from the interferometer. In certain embodiments, the surface of the solid growth medium has a non-zero root mean squared roughness value less than or equal to 200 nm, 125 nm, 100 nm, or 50 nm.

In some embodiments, a non-transitory computer readable storage medium stores one or more programs, the one or more programs comprising instructions, which when executed by one or more processors of an electronic device comprising, or operably connected to, a vertical scanning interferometer, cause the device to acquire a 3D profile with a height measurement of a microcolony grown on a surface and to compute a sample parameter based on the 3D profile with the height measurement. The microcolony can comprise a microbial colony forming unit (CFU). In certain embodiments, the sample parameter is one of microcolony height, aspect ratio, volume, number of microcolonies, microcolony morphology, microcolony count, or a combination thereof. In certain embodiments, the programs can further cause the device to identify species kind of the microbial CFU, determine microbial CFU population value in a microcolony, estimate a growth rate value of the microbial CFU, provide a positive/negative outcome of a diagnostic test, indicate a biofilm state, or perform a combination thereof based on one or more of the sample parameters.

In some embodiments, an apparatus comprises a vertical scanning interferometer configured to probe a growth plate at a region comprising a growth medium on which a biological sample is deposited, the growth medium having a non-zero root mean squared roughness value less than or equal to 200 nm. A sample holder can be configured to hold the growth plate. A processor can be configured to obtain a 3D profile with a height measurement of a microcolony comprising microbial CFUs from the biological sample, and to calculate a sample parameter based on the 3D profile. In certain embodiments, the vertical scanning interferometer can have a sampling area at the sample that is less than or equal to 10 mm, 8 mm, 5 mm, 3 mm, or 1 mm across. In certain embodiments, the growth plate can comprise a plurality of samples having a separation therebetween. According to one example, the growth plate can comprise a plurality of wells for containing samples. In certain embodiments, the sample holder can comprise a motorized translation stage to adjust the position of the growth plate and allow different regions and/or different wells to be probed by the vertical scanning interferometer.

The purpose of the foregoing summary and the latter abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. Neither the summary nor the abstract is intended to define the invention of the application, which is measured by the claims, nor is it intended to be limiting as to the scope of the claims in any way.

BRIEF DESCRIPTION OF THE DRAWINGS

FIG. 17 is a flow chart showing analysis steps for WLI data. Steps 1-4 are standard practice for turning raw imaging data into 3D surface profiles. Steps 5-8 describe surface profile analysis steps that are typically used with surface profile data. The specific combination of steps 5-8 are an embodiment of the methods described herein. The order of steps 5-8 may be changed. The purpose of steps 5-8 is to create a surface profile image where the signal from microbial colonies of interest are distinct and detectable from a flattened and smoothed background.

FIG. 18 is a flow chart showing further analysis steps that are carried out in some embodiments on data that has already been processed through the analysis steps of FIG. 17. The purpose of these analysis steps is to search for and identify peaks in the surface profile data that could be microbial colonies and then further filter the set of peaks to reduce the rate of errant identifications. Further analysis can include calculation of parameters based on the set of features identified as microbial colonies, application of all prior analysis steps to a series of images, and calculation of parameters based on the series or trends in the series.

DETAILED DESCRIPTION

Figure 1:
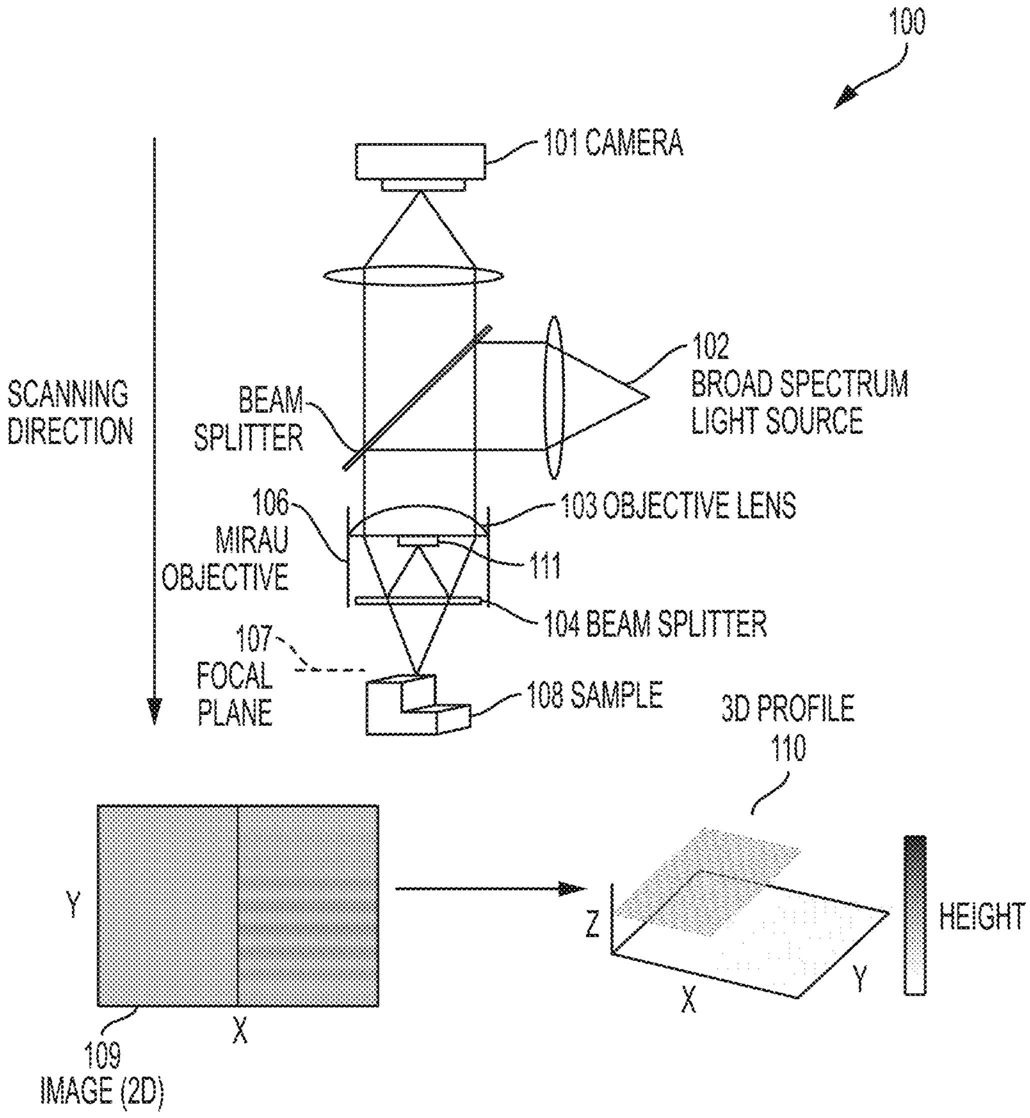
FIG. 1 is a schematic diagram of a system for characterizing and counting cells and microcolonies according to embodiments described herein.

Embodiments described herein can employ high-resolution measurements of height variations over large lateral areas, which height variations can be as small as the sub-nanometer scale, in order to characterize and/or enumerate microbiological growth on solid media in hours rather than days. Often, the characterization and/or enumeration of microcolonies is possible before they are visible to the naked eye and even when height variations are smaller than the diffraction limited resolution of the illumination source. This would be valuable because it could allow practitioners to receive results more rapidly than current methods. If used in a medical setting this would mean having diagnostic results more quickly. As used herein, a microcolony can refer to a microbial CFU (e.g., a cell), or a colony of microbial CFUs, having such qualities and/or such small dimensions that the microcolony cannot yet be seen with the naked eye. In non-limiting examples, a microcolony can have non-zero dimensions less than 50 μm, 30 μm, 25 μm, 15 μm, 10 μm, or 6 μm.

The inventors have determined that the problem of long delays commonly associated with detecting and counting microbial colony forming units (CFUs) can be solved by non-destructively acquiring a three-dimensional (3D) profile of a CFU on a solid growth medium by vertical scanning interferometry. The 3D profile includes a high-resolution height measurement. Solid growth medium, as used herein, can refer to a non-liquid medium and can include a semi-solid medium (e.g., a gel). One example of a solid growth medium includes agar. Unexpectedly, the surface flatness of the growth medium can be prepared with sufficient smoothness for compatibility with vertical scanning interferometry techniques.

Vertical scanning interferometry is a surface imaging technique, but it cannot resolve continuously through the depth of a sample. White light interferometry (WLI) is an example of vertical scanning interferometry and has been optimized for applications with stable, hard reflective surfaces. As a result, application of WLI to dynamic, wet samples that often have relatively rougher surfaces and are typical of in vitro imaging in microbiology (such as described herein) is challenging and non-intuitive. However, the inventors have determined that counting and characterization of small, microbial colonies can be performed successfully using vertical scanning interferometry and WLI. The imaging techniques are used to collect surface profiles of colonies on a biological growth medium at a particular time, or over a range of time, at high axial (i.e., depth or height) resolutions. WLI is capable of providing high depth resolution at low magnification, which unexpectedly enabled simultaneous imaging of hundreds of microcolonies that were accurately enumerated within the early hours after plating. It was not necessary to wait for days for visual identification with the naked eye. Furthermore, high depth resolution at high magnification enables observation and study of individual microcolonies and/or CFUs composing those microcolonies, which can enable highly accurate measurement of microbial CFU morphology, colony morphology, colony growth dynamics, and growth rate. In certain embodiments the sample parameters and values based on the sample parameters can be determined within a non-zero length of time that is less than or equal to 1 hour, 2 hours, 4 hours, 6 hours, 8 hours, 10 hours, 12 hours, or 18 hours after plating (i.e., introducing) a biological sample potentially having a microbial CFU on the solid growth medium.

As utilized in embodiments described herein, vertical scanning interferometry does not operate on the principle of differences in optical path lengths through cells and liquid media. Rather, embodiments described herein use vertical scanning interferometry to image cells, microbial colonies, and microcolonies grown on surfaces of plates comprising a solid growth medium. For example, in the WLI instrument illustrated in FIG. 1, an objective lens 103 can have either a Michelson-type, Mirau-type, Linnik-type, or Twyman-green interferometer 106. WLI utilizes a broad-spectrum light source 102. The light source has a short coherence length so that interference only occurs when the length of the measurement beam and reference beam are nearly matched. WLI can be called coherence scanning interferometry, coherence probe microscope, coherence scanning microscope, coherence correlation interferometry, Mirau correlation microscope, white light interferometry, white light scanning interferometry, scanning white light interferometry, white light scanner, white light phase shifting interferometry, and vertical scanning interferometry. Images of interference patterns 109 arise at the image sensor 101 when light reflected from the sample 108 is combined with light reflected from a mirror 111 in the reference arm of the interferometer. The short coherence length of the illumination means that interference only occurs when the sample 108 at the focal place 107 and the reference mirror 111 are nearly equidistant from the beam splitter 104. Thus, recording images while scanning the instrument's optics vertically results in the appearance of characteristic interference fringe patterns that correspond with vertical heights in the sample 108. Analysis of the series of images results in a 3D profile 110 of the surface with 3-5 nm resolution in the Z-direction (i.e., height resolution). In some embodiments, the resolution can be 0.5 nm to 50 nm, 3 nm to 50 nm, 10 nm to 50 nm, or 3 nm to 10 nm. The resolution in the X-Y plane is diffraction limited.

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Non-transitory as used herein when referring to a computer-accessible medium, is a limitation of the medium itself (i.e., tangible, not a propagating electromagnetic signal) as opposed to a limitation on data storage persistency. The term is not intended to otherwise limit the type of physical computer-readable storage device that is encompassed by the phrase computer-accessible medium or memory. For instance, the terms "non-transitory computer readable medium" or "tangible memory" are intended to encompass types of storage devices that do not necessarily store information permanently, including but not limited to, computer-readable media that store data only for short periods of time and/or only in the presence of power, such as register memory, processor cache and Random Access Memory (RAM). Program instructions and data stored on a tangible computer-accessible storage medium in non-transitory form may further be transmitted by transmission media or signals such as electrical, electromagnetic, or digital signals, which may be conveyed via a communication medium such as a network and/or a wireless link.

Figure 2:
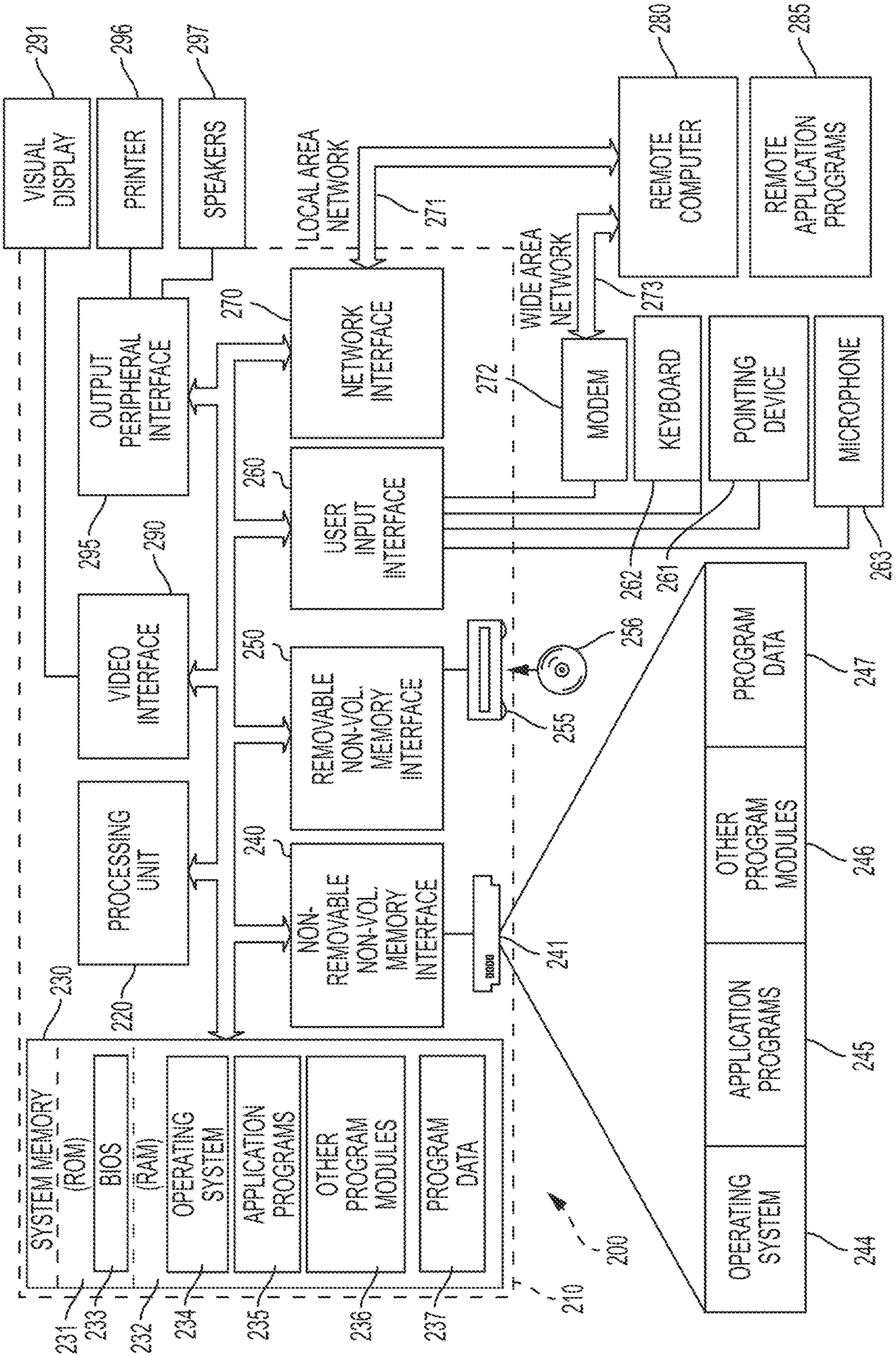
FIG. 2 is a schematic diagram of a computing environment according to aspects of embodiments described herein.

FIG. 2 is one embodiment of a computing environment to which a vertical scanning interferometer can be operably connected. Alternatively, the computing environment can be integrated with a vertical scanning interferometer. In one example, a computing environment such as shown in FIG. 2 can be used to control operation of WLI system 100. The computing environment can further be used to acquire a series of 2D images (e.g., with some containing interference patterns 109 from a camera 101) and to process the images into 3D profiles 110.

With reference to FIG. 2, an example system for implementing some embodiments includes a general-purpose computing device in the form of a computer 210. Components of computer 210 may include, but are not limited to, a processing unit 220 (which is not limited to CPUs, but can comprise GPUs), a system memory 230, and a system bus 221 that couples various system components including the system memory to the processing unit 220. The system bus 221 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. Memory and programs described herein be deployed in corresponding portions of FIG. 2.

Computer 210 typically includes a variety of computer readable media. Computer readable media can be any available media that can be accessed by computer 210 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, sash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 210.

Communication media typically embodies computer readable instructions, data structures, program modules or other data in a transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

The system memory 230 includes computer storage media in the form of volatile and/or nonvolatile memory such as read only memory (ROM) 231 and random-access memory (RAM) 232. A basic input/output system 233 (BIOS), containing the basic routines that help to transfer information between elements within computer 210, such as during startup, is typically stored in ROM 231. RAM 232 typically contains data and/or program modules that are immediately accessible to and/or presently being operated on by processing unit 220. By way of example, and not limitation, FIG. 2 illustrates operating system 234, application programs 235, other program modules 236, and program data 237.

The computer 210 may also include other removable/nonremovable volatile/nonvolatile computer storage media. By way of example only, FIG. 2 illustrates a hard disk drive 241 that reads from or writes to non-removable, nonvolatile magnetic media, and an optical disk drive 255 that reads from or writes to a removable, nonvolatile optical disk 256 such as a CD ROM or other optical media. Other removable/non-removable, volatile/nonvolatile computer storage media that can be used in the exemplary operating environment include, but are not limited to, magnetic tape cassettes, sash memory cards, digital versatile disks, digital video tape, solid state RAM, solid state ROM, and the like. The hard disk drive 241 is typically connected to the system bus 221 through a nonremovable memory interface such as interface 240, and optical disk drive 255 are typically connected to the system bus 221 by a removable memory interface, such as interface 250.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The drives and their associated computer storage media discussed above and illustrated in FIG. 2, provide storage of computer readable instructions, data structures, program modules and other data for the computer 210. In FIG. 2, for example, hard disk drive 241 is illustrated as storing operating system 244, application programs 245, other program modules 246, and program data 247. Note that these components can either be the same as or different from operating system 234, application programs 235, other program modules 236, and program data 237. Operating system 244, application programs 245, other program modules 246, and program data 247 are given different numbers here to illustrate that, at a minimum, they are different copies.

A user may enter commands and information into the computer 210 through input devices such as a keyboard 262, a microphone 263, and a pointing device 261, such as a mouse, trackball or touch pad. Other input devices (not shown) may include a joystick, game pad, satellite dish, scanner, or the like. These and other input devices are often connected to the processing unit 220 through a user input interface 260 that is coupled to the system bus, but may be connected by other interface and bus structures, such as a parallel port, game port or a universal serial bus (USB). A visual display 291 or other type of display device is also connected to the system bus 221 via an interface, such as a video interface 290. Video interface 290 can comprise a graphics card having a GPU. The GPU can be used for computations. In addition to the monitor, computers may also include other peripheral output devices such as speakers 297 and printer 296, which may be connected through an output peripheral interface 295.

The computer 210 is operated in a networked environment using logical connections to one or more remote computers, such as a remote computer 280. The remote computer 280 may be a personal computer, a hand-held device, a server, a router, a network PC, a peer device or other common network node, and typically includes many or all of the elements described above relative to the computer 210. The logical connections depicted in FIG. 2 include a local area network (LAN) 271 and a wide area network (WAN) 273, but may also include other networks. Such networking environments are commonplace in offices, enterprise-wide computer networks, intranets and the Internet.

When used in a LAN networking environment, the computer 210 is connected to the LAN 271 through a network interface or adapter 270. When used in a WAN networking environment, the computer 210 typically includes a modem 272 or other means for establishing communications over the WAN 273, such as the Internet. The modem 272, which may be internal or external, may be connected to the system bus 221 via the user input interface 260, or other appropriate mechanism. In a networked environment, program modules depicted relative to the computer 210, or portions thereof, may be stored in the remote memory storage device. By way of example, and not limitation, FIG. 2 illustrates remote application programs 285 as residing on remote computer 280. It will be appreciated that the network connections shown are exemplary and other means of establishing a communications link between the computers may be used.

EXAMPLES AND COMPARISONS

To further illustrate certain embodiments of the disclosed methods, systems, and non-transitory computer readable media, and to provide various comparative analyses and data, below are some examples with comparison test data.

WLI was used to speed CFU enumeration of cells and bacterial colonies, as well as determine growth rates, on agar by observing them before they can be seen or quantified with traditional methods. We non-destructively measured surface protrusions caused by individual bacteria and microcolonies on the surfaces of agar plates with the high resolution capabilities of WLI. Gram-negative bacterium *Pseudomonas fluorescens* (PF) and the Gram-positive bacterium *Bacillus thuringiensis* (BT) were used. Both PF and BT are model organisms that share many of the microbiological characteristics of other pathogenic bacteria. PF is often used to model biofilm formation and as a surrogate for *Pseudomonas aeruginosa*—a pathogen that is associated with cystic fibrosis, pneumonia, and sepsis. BT is used as a bench-safe model for studying certain attributes of anthrax spore dispersal. The use of these bacterial species in the following examples is not intended to be limiting. The invention may be applied with a wide variety of microbial species, including bacteria, fungi, and archaea. The results described below indicate that embodiments disclosed herein are capable of accurate enumeration of CFU counts from agar plates while also enabling accurate characterization and quantification of other morphological and phenotypic attributes.

WLI Instrument and Software:

WLI surface profiles were measured by a white-light interferometer operated in vertical scanning mode. Measurements were made using a range of interferometric objective lenses (2.5× to 50×) with 0.55×-2.0× field of view magnifying lenses. Imaging area ranged from 4.6×3.4 mm at the largest to 62×47 μm at the smallest. As mentioned elsewhere, additional imaging area sizes can be utilized via alternative configurations of lenses. A green LED was used for illumination in order to maximize horizontal resolution. The noise threshold was set to the minimum value, 0.001. Both Michelson-type and Mirau-type interferometric objective lenses were used. No compensation was used when imaging through thin glass coverslips. The low magnification lens could tolerate a small mismatch in optical path length between the arms of the interferometer. Image acquisition and instrument control were performed with the instrument's control and analysis software.

Bacterial Strains and Antibiotics:

*Pseudomonas fluorescens* subsp. *Migula* (ATCC 12525) and *Bacillus thuringiensis* subsp. *kurstaki* HD1 (*Bacillus* Genetic Stock Center, Columbus, Ohio) were streaked onto lysogeny broth (LB) agar plates and incubated at room temperature for 2 days. Bacteria from isolated colonies were next grown overnight (~18 hrs) at 26° C. 225 rpm in 3 ml of liquid LB broth. The concentration of bacteria in the resulting culture, as measured by the method described herein and by traditional plate-counting method, was between $5\times10^8$ CFU/ml and $4.5\times10^9$ CFU/ml.

Bacterial Agar Plating and Enumeration:

For WLI imaging multiple 2 μl drops of bacteria in LB broth at $10^{-3}$ to $10^{-5}$ dilutions were carefully deposited onto pre-poured Trypticase™ Soy Agar (TSA) plates (BD Biosciences, 221283). For some high-resolution imaging of single colonies, 2 μl drops were spotted onto self-poured LB-agar plates in which agar medium was poured to almost the top of the petri dish so that the objective could be positioned appropriately. Additionally, 200 μl of each dilution was spread-plated in quadruplicate on TSA plates so that traditional CFU spread-plating enumeration could be compared to CFU enumeration by WLI.

WLI Imaging:

In WLI imaging, a beam splitter divides the spectrally-broadband visible wavelength light (white light) LED source into two parts where the reference beam is reflected from a mirror while a measurement beam reflects off the object of interest. Optical interference occurs in the viewing area of the measured surface when the optical path length between the reference and measurement beam are nearly identical. Interference patterns appear during a portion of a vertical scan because the distance to the sample is changing. Images are recorded in ~100 nm steps and interference fringes typically appear over 5-10 μm of vertical scanning distance. Intensity at each pixel in a Z-correlated image stack is analyzed to extrapolate the vertical position of each X-Y location, resulting in a topographical surface map. Unexpectedly, the height measurement (i.e., image intensity as a reflection of z-direction position or distance) assisted in detection of microcolonies, which facilitated early enumeration and characterization before the cells and microcolonies were observable or quantifiable by other means (e.g., visual detection by the naked eye).

Image Processing and Analysis:

Reconstruction of 3D surface profiles from raw image data was performed by surface imaging and metrology software following the process shown in FIG. 17. Steps 1-4 in FIG. 17 are standard practice for turning raw imaging data into 3D surface profiles and were performed by instrument software. Data pre-treatment and analysis was performed by software, including but not limited to leveling the data to remove planar, spherical, and cylindrical form and other types of background. Steps 5-8 of FIG. 17 describe surface profile analysis steps that were used in these examples, with the purpose of creating a surface profile data set where the signal from microbial colonies of interest are distinct and detectable from a flattened and smoothed background. The order of steps 5-8 may be changed. In this example the data was levelled and smoothed to remove curvature and planar tilt. When necessary, a mask was applied to regions that were not suitable or not of interest. Data under the mask were excluded from further analysis and effectively removed from the image. A data filling algorithm was applied to restore intermittent gaps in the surface where there was not sufficient interference to determine the vertical position of the surface. To resolve a surface or interface with white light interferometry the surface must be at least partially reflective. Non-reflective surfaces will not return enough light back to the microscope objective to generate measurable fringe contrast. For the same reason samples or sample features with steep slopes will often not reflect in the direction of the objective lens and are not measurable. In these cases, the resulting profile image will have points or regions of missing or distorted data, although usually a great deal can still be inferred from incomplete renderings. Step 8 of the process shown in FIG. 17 is the smoothing of fine details with Gaussian regression filters, Fourier filters, combinations of these or others with options for high pass, bandpass, low pass or combinations of these.

Once the analysis steps of FIG. 17 was completed further analysis was conducted to identify, count, and characterize microbial cells and colonies, as shown in the flow chart in FIG. 18. As described in Step 1 of FIG. 18 CFU enumeration was conducted by searching for regions in the data sets that have peak values over neighboring regions that are greater than a threshold that is a defined multiple (or fraction) of the size of a microbe of interest. This creates a list of potential microbial colonies. In Step 2 of FIG. 18 this list is filtered to remove regions that are outliers on one or more parameter that is measured for each region. This removes regions that are unlikely to be true microbial colonies (e.g., single pixel features, indentations in the agar, etc.). The measured parameters may include height, area, volume, morphology, roughness, or others. At the conclusion of Step 2 of FIG. 18 there is a list of regions in the 3D data that likely are microbial colonies. It is never possible identify every microbial colony or to avoid including some non-microbial features; however, this analytical process was designed to reduce errors to a reasonable minimum. Further analysis and calculation of parameters may be conducted using the set of microbial colony regions. In one case, the regions are counted to give the CFU on the plate. The number of colonies in the original liquid culture can also be calculated by converting to CFU/ml using a factor for the culture volume and dilution. Additional parameters that can be calculated for each of the regions (or as an average over the whole group of regions of interest) include but are not limited to projected surface area, volume of all regions, average volume of regions, height of regions, average height of regions, surface roughness of regions, shape of regions and other morphological features of each colony visible in the image. The full analytical process (steps shown in FIG. 17 followed by steps 1-3 of FIG. 18) can be repeated on multiple data sets or images in a series. As described in steps 4 and 5 in FIG. 18, more parameters can be calculated based on series of images. Statistical averages and other parameters from multiple samples may be calculated. If the images are collected over time then the time series also enables calculation of growth rates, doubling times, rates of decline, rates of inhibition, time-kill curves, and other time-dependent parameters.

Figure 3:
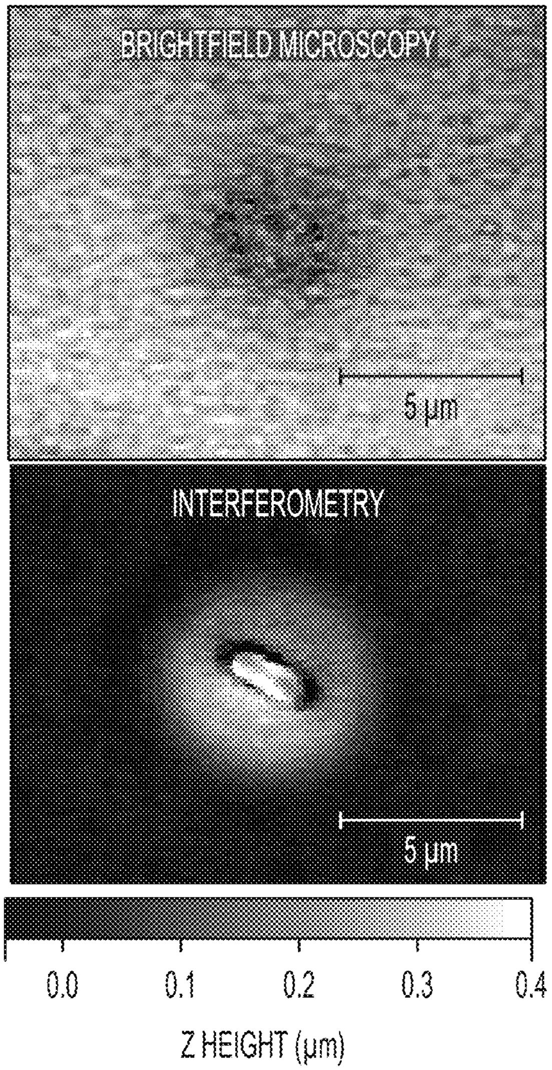
FIG. 3 is a comparison of a standard brightfield optical microscope image (top) with an interferometric microscopy image (bottom) of a single cell of *Pseudomonas fluorescens*. The interferometric image resolves z-height variations of less than 0.4 microns that make the microbe's size and shape more clear than in the standard optical image. The interferometric image is shaded by z-height according to the scale shown below the image.

Referring to FIG. 3, we compared 2D optical and 3D interferometric images of a sample of PF on the surface of an agar plate. This figure illustrates that WLI 3D imaging with fine vertical resolution also improves clarity in the X-Y plane and makes it easier to resolve the shape and size of small microbes on agar plates at the single cell level. WLI clearly shows in FIG. 3 that the size and morphology of individual cells on a surface can be accurately imaged and measured—something typical microscopy is challenged to do, particularly with large imaging areas. The volume of a single microbe may be as small as ~1 femtoliter ($10^{-15}$ l or 1 $\mu m^3$) but the theoretical volumetric resolution of WLI (5 nm height change from a single pixel at high magnification) is ~50 zeptoliter ($5\times10^{-20}$ l). As a result, there is high confidence that embodiments described herein can accurately resolve the small volume changes that result from cell division and multiplication.

Figure 4:
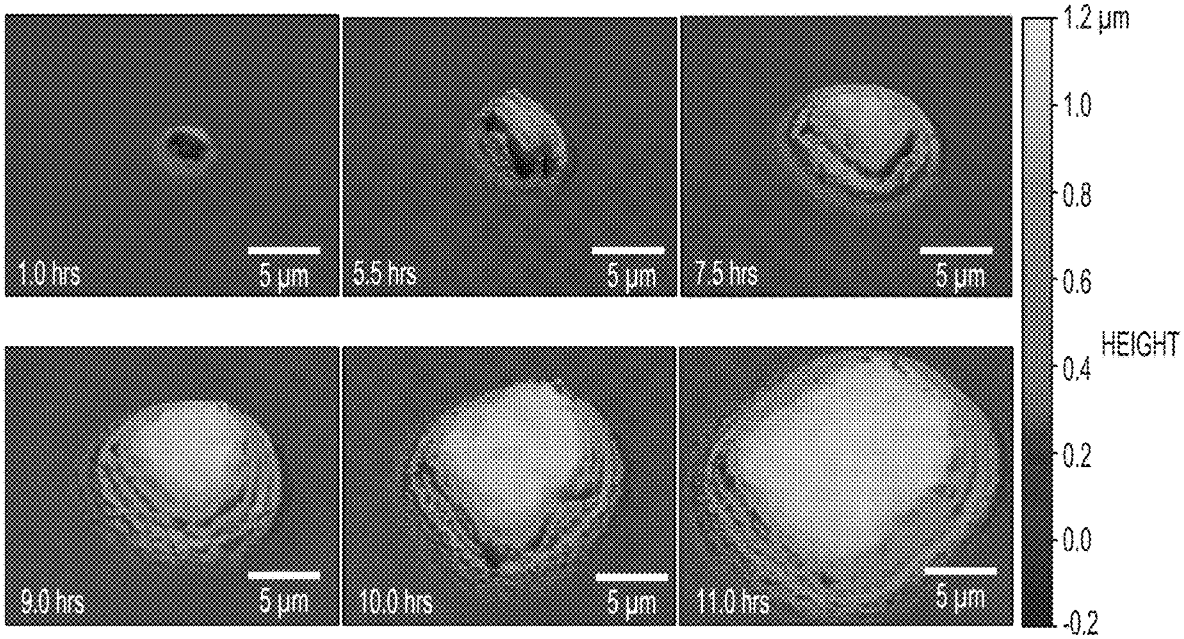
FIG. 4 includes a series of WLI surface profiles of a single *Pseudomonas fluorescens* colony on an agar plate showing growth from a single colony 1 hr after plating to a multicellular microcolony at 11 hrs. Features that are below the diffraction limit appear to show outlines of individual bacteria. Horizontal scale is shown with a bar in each image. Vertical scale is represented by the gradient scale on the right.

The microbe shown in FIG. 3 was allowed to continue to grow and was imaged at regular intervals. FIG. 4 shows a series of high magnification 3D optical profile images of a PF sample that were captured as the single microbe grew into a microcolony. In the early hours (approximately 1-6 hrs), it was possible to observe individual cells multiplying. At the 9, 10, and 11 hour time points shown in FIG. 4 the morphology of the cells are also clearly visible at the surface of the colony. The cells have traditional rod-like shapes. The colony appears to grow uniformly in all directions, which is consistent with the phenotype of PF plate colonies that grow into a rounded ball-like shape after about 24 hours. FIG. 4 shows that embodiments described herein enable non-destructive imaging of the surface morphology of early-stage microcolony growth.

Figure 5:
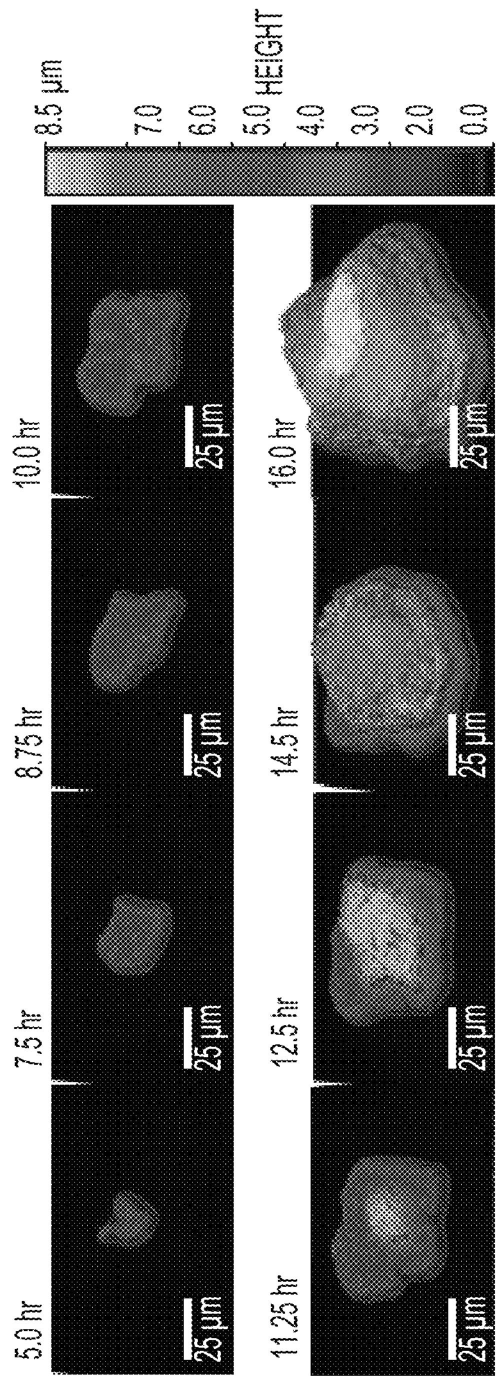
FIG. 5 is a series of WLI surface profiles of a single *Bacillus thuringiensis* colony on an agar plate showing growth of a small irregularly shaped colony 5 hr after plating. The microcolony grew laterally in the first 10 hrs before a second bacterial layer emerged at 11.25 hrs. The height of each layer is approximately 2 microns. Lateral scale is shown with a bar in each image. Vertical scale is represented by the gradient scale on the right.

FIG. 5 shows a series of high magnification images of BT grown on an agar plate. A different morphology was observed for this species compared to PF shown in FIG. 4. The BT microcolony seen at 5 hrs is irregularly shaped and appears to grow laterally in a single-layered plate for more than 10 hours before a second layer of microbes emerges. A third layer of microbes is visible at 14.5 hours. In other attempts to image BT we began imaging at 1 hr, as was done for PF in FIG. 4, but this was not successful. Interestingly, the colony did not grow unless it was first incubated in a closed agar plate for 5 hrs. Of note, imaging was performed with an open plate—exposing the bacteria to a dry environment. It is possible that the microbe could not thrive and establish a colony under these arid conditions. If BT was pre-incubated for 5 hrs while covered the colony was established well enough to allow continued growing for the rest of the experiment in arid conditions. Accordingly, in some embodiments, the growth medium comprises an enclosure or lid facilitating a controlled environment.

Figure 6A:
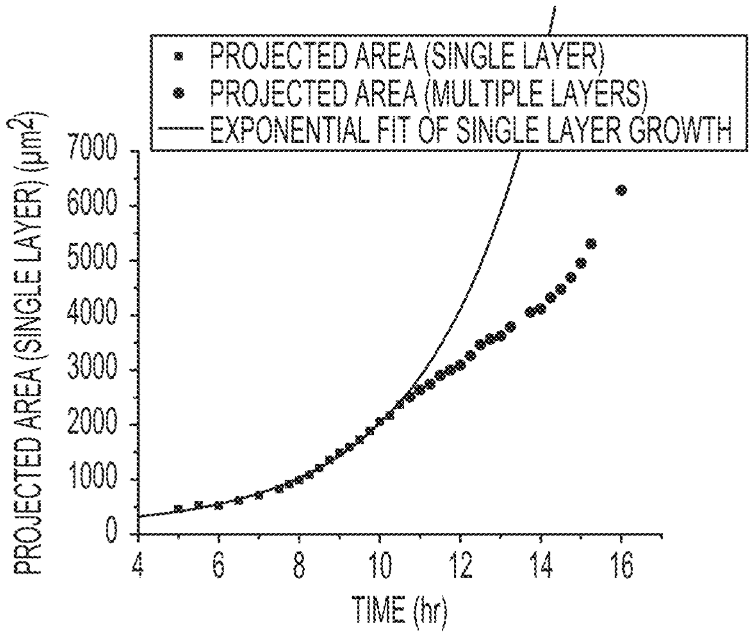
FIGS. 6A and 6B include charts growth of a single BT colony as measured and calculated from the change in (6A) projected area and (6B) volume over time. Data were collected from 37 WLI surface profile images over 16 hours. Data show that measuring colony volume with methods described herein is a more accurate way to track microbial growth than by using projected area of the colonies.
Figure 6B:
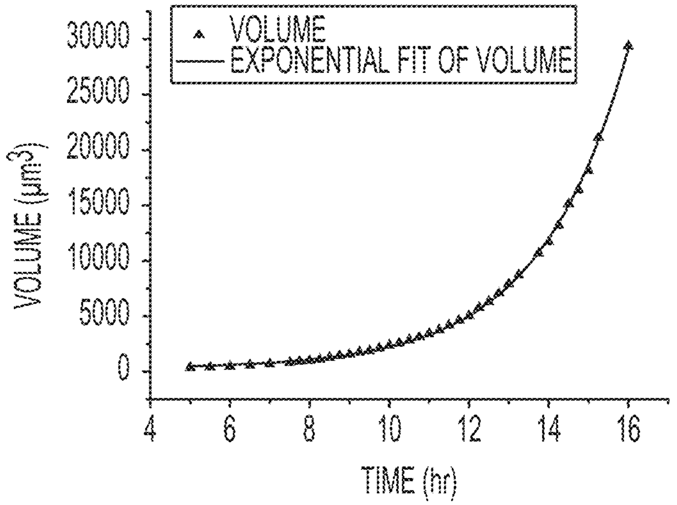

The image series in FIGS. 4 and 5 clearly show development and growth of morphological changes in the early stages of colony formation and illustrate the ability to measure growth without disrupting or interrupting growth of the colony. Unexpectedly, the image data can also be used to quantify growth rate by observing changes in the volume of a colony over time. FIG. 6 shows the calculated/projected measured area and volume of a single BT colony as measured from the images shown in FIG. 5. Bacterial growth by cellular division and growth rates are shown to be exponential, as expected. FIG. 6A shows that measuring growth by simple observation of lateral expansion (projected area) appears to be an accurate measure of growth rate in the early hours, when the colony grows laterally. However, the inventors determined, unexpectedly, that when a second layer of microbes emerges around 11 hrs, the projected area no longer follows an exponential growth curve. By comparison, FIG. 6B shows that the volume, calculated from WLI data, matches the exponential growth of bacteria throughout the experiment. In this case, the 3D measurement enabled by WLI enabled more accurate measurement of microbial growth through the duration of the experiment. Accordingly, embodiments described herein are able not only to detect microcolonies earlier that conventional approaches, but also to more accurately characterize sample parameters including, but not limited to microcolony volume, bacteria population value, bacterial growth rate, and number of microcolonies. Bacterial growth rate is a key value since it allows differentiation between bacteria species. For example, WLI could be used to identify aggressive/fast growing bacterial species.

Fitting the volume data with an equation for exponential growth resulted in a growth constant (k) of 0.40, which indicates a doubling time (T) of 1.7 hrs. The fitting data also indicate an initial volume of 33.8 $\mu m^3$, which may be interpreted as the volume of a single microbe. Thus at 5 hrs there may be as few as 8 bacteria in the colony (though the measured volume at 5 hrs indicates that there may be a few dozen because the initial growth rate is higher in incubation). These data show another valuable way to use WLI data of growing bacteria colonies. The volume of individual microbes can be calculated as well at the time needed to replicate. The data show that it is possible to image BT colonies with as few as 8 cells. A similar analysis of images of PF indicate that a single cell can be observed.

Figure 7:
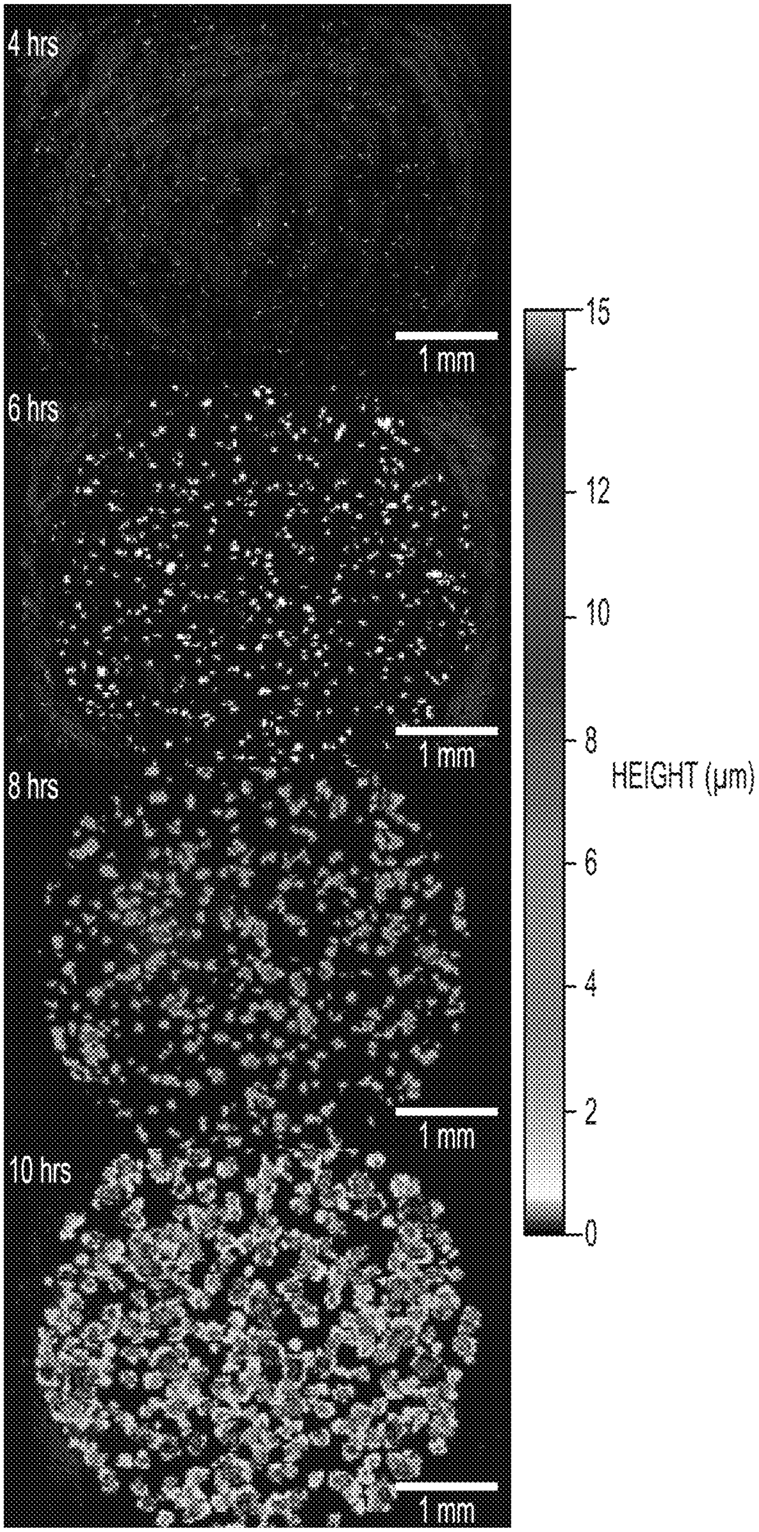
FIG. 7 includes a series of 3D surface profile images of 2 μl spots of diluted culture of *Bacillus thuringiensis* showing the growth of many microcolonies over time. Lateral scale as shown by the bar in each image. Vertical scale is represented by the gradient scale on the right. The methods described herein enable observation of a large number of small colonies over a large field of view (relative to traditional microscopy methods).
Figure 8:
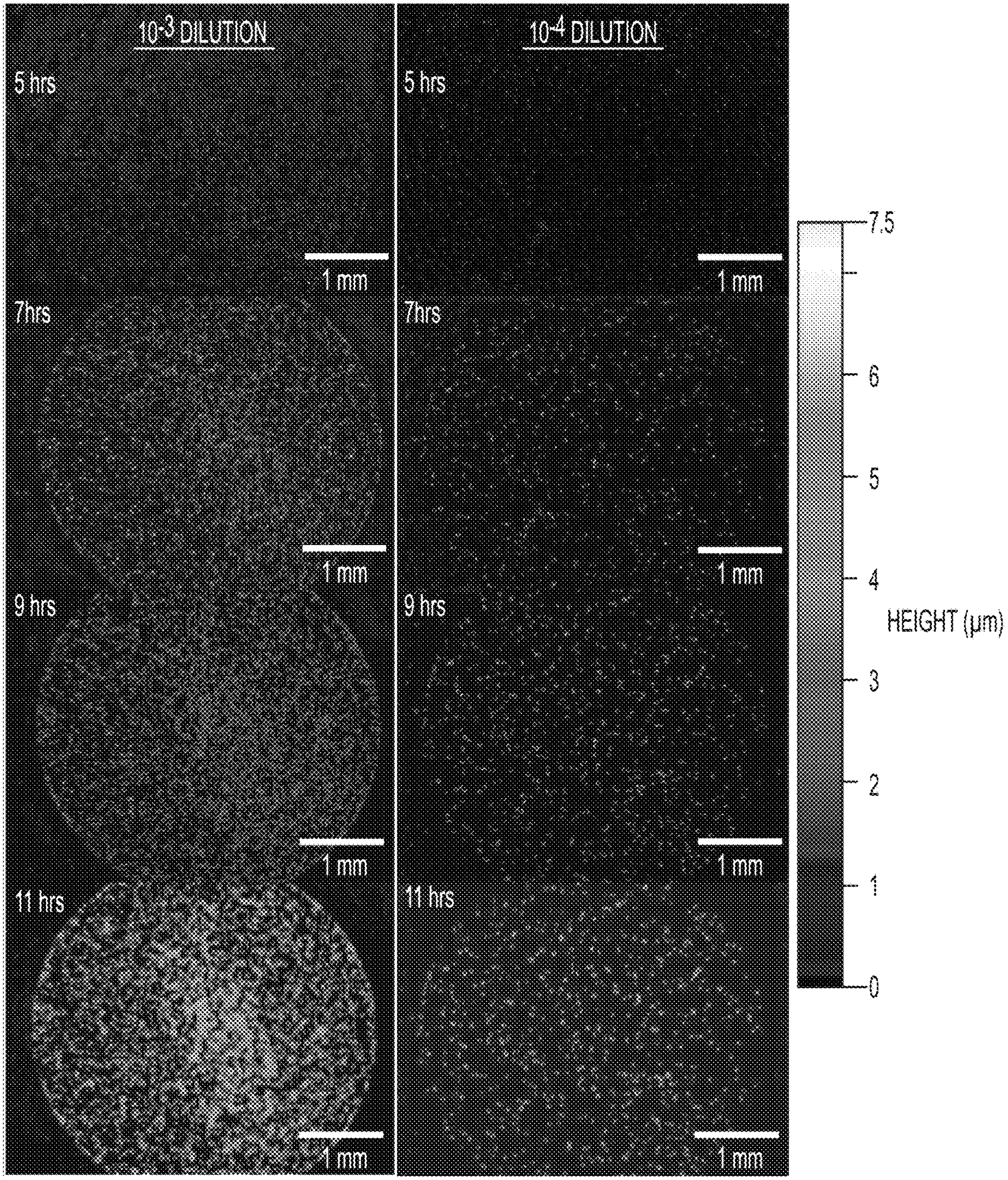
FIG. 8 includes a series of 3D surface profile images of 2 μl spots of diluted culture of *Pseudomonas fluorescens* showing the growth of many microcolonies over time. The culture imaged on the left was diluted by three orders of magnitude ($10^{-3}$) while the same culture diluted by four orders of magnitude ($10^{-4}$) is shown on the right. The images show hundreds of microcolonies growing (and merging). Lateral scale as shown by the bar in each image. Vertical scale is represented by the gradient scale on the right.

A limitation of the data shown in FIGS. 3 and 4 is that it only shows or derives information from a single colony imaged at high magnification. This was used to capture detailed images but does not show the capability for analysis of variation among multiple colonies that may be present on the culture. Embodiments described herein have the unique ability to maintain high axial (vertical) resolution even at low magnification (enabling large field of view for analysis). To demonstrate this capability and how it relates to measurement of multiple colonies on cultures BT and PF cultures were monitored with the widest possible field of view as a function of time (FIGS. 7 and 8). A diluted culture was pipetted onto the agar plates a small volume was used (2 μl) in order to make a spot on the plate that could be imaged nearly in its entirety in one field of view. Bacteria spread evenly across ~5 mm diameter discs creating miniature replicates of full scale agar plates (typically 100 mm diameter). Under normal circumstances it would not be possible to monitor, measure, and enumerate colony forming units in a 5 mm disc because the colonies would grow too large and merge together before they became visible. But with embodiments described herein, it is possible to do so by collecting a single 3D surface profile image containing all of the colonies and to do so very soon after plating. This capability, made possible by the invention described herein, enables more many more samples in the same amount of space, supports automation of biomedical processes and significantly reduces process waste/expense. As a result of this invention it would be possible to modify current bacterial plate culture assays and tests by substituting WLI imaging and analysis in place of manual plate counting. Doing so could reduce the amount of plate culturing materials (agar, plates, etc.) by a factor of 100 and also reduce the space needed and energy needed for storage and processing by a similar amount. FIGS. 7 and 8 show a selection of images from series taken over time of plated spots of BT and PF, respectively. The images show a constellation of hundreds of microcolonies as they grow and eventually merge together. The characteristic irregular shapes of BT colonies and emergence of multiple layers are as visible in the overview image as in the high-resolution view. FIG. 8 includes images of PF at two culture dilutions. The more dilute culture is barely visible in the early hours, owing to the small number of colonies, but this did not hinder further analysis of colony morphology and enumeration of CFUs in the culture because the technology provides a combination of high vertical resolution and image processing of the sample that can isolate protruding colonies from the background agar. In fact, further analysis was conducted with a solution that was further diluted ($10^{-5}$) by another order of magnitude. The reduced number of colonies in the imaging spot made it less likely that colonies would merge and overlap at later times. Analysis algorithms did not have to be modified to accommodate a low number of sparse colonies in an image.

Figure 9A:
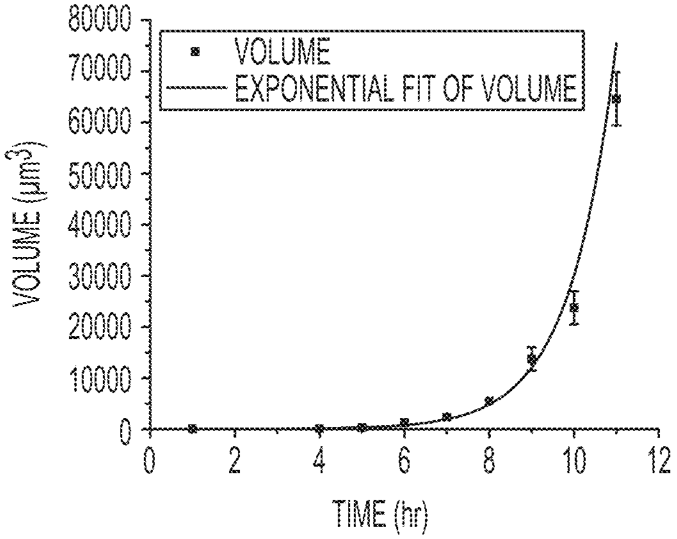
FIGS. 9A and 9B include graphs of the measured volume of multiple microcolonies of *Bacillus thuringiensis* (9A) and *Pseudomonas fluorescens* (9B) grown on agar plates over a period of 11 hours. Each species follows an exponential growth curve as shown by red fit lines. The *Bacillus* colonies grew more quickly than did the *Pseudomonas* colonies. Error bars show standard deviation from ~60-80 microcolonies shown in each wide-field-of-view image.
Figure 9B:
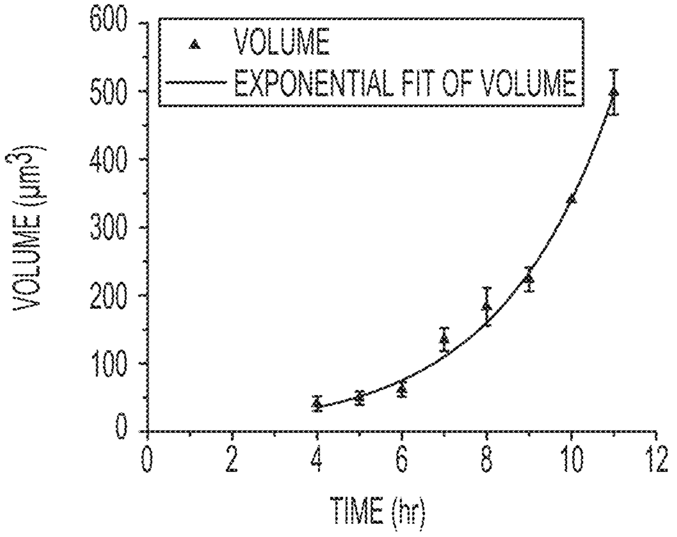

The growth of BT and PF colonies in FIGS. 7 and 8 were further analyzed by counting the colonies in each image and measuring the volume of each colony. There were 87.3±5.5 colonies present in PF images collected at the $10^{-5}$ dilution. Analysis was also done for a lower dilution at some earlier times (when the colonies were well separated) with upwards of 800 colonies in a single image. Images of BT also contained between 50 and 750 separate microcolonies, depending on the dilution of the culture prior to plating. These data show that the methods described herein can distinguish and count a large number of microbial colonies in a small area. This is useful for rapid enumeration as samples could be added to plates without the time-consuming process of preparing dilutions. However, employing dilution to reduce the number of colonies in an image is still preferable when measuring growth rate in order to avoid colony merging as the bacteria multiply. In both of the cases shown in FIG. 9, it was clear that volumetric measurements showed the expected exponential growth trend. The growth curves in FIG. 9 indicate that BT grew faster than PF, which is a feature of this invention that could be used to distinguish different species. BT grew fast when a large area was observed then when high-resolution imaging tracked the growth of a single colony (FIG. 6). This is likely because in this experiment it was possible to maintain a lid on the agar plate most of the time. The lid was only removed during the imaging process. The lid may have limited desiccation of the sample by maintaining a higher local humidity. These analyses and the data shown in FIGS. 7-9 clearly demonstrate that it is possible to accurately measure the morphology and growth of many hundreds even thousands of microcolonies that are all growing in a relatively small area (~5 mm diameter disc) with WLI microscopy. This invention enables the use of microscopy to count microbial colonies over a relatively large area because typical microscopy approaches would require using a high magnification and that would result in a relatively small imaging area.

Nonetheless, it is not a trivial exercise to enumerate the colonies in wide field WLI images of culture spots. The bacteria are small, and they do not protrude very far above the surface of the agar in the plate. For example, it was determined that in the earliest hours the PF culture protruded from the agar by as little as 125 nm. Complicating the measurement is the uneven surface of the growth media. In some embodiments, the root mean squared roughness of the growth media as measured with WLI is less than 200, 100 or 50 nm. To mitigate the uneven surface of the growth media the analysis routine was used to distinguish microbes and small colonies from the surrounding agar. The analysis routine utilized localized/regional differences in height change about a microbial colony and not a generalized surface average. The analysis searched for peak regions above the background by calculating surface statistics from multiple "islands" of data in each sample. Filters and some manual selection were applied to remove data that was incorrectly labeled (e.g., single pixel peaks or excessively large regions).

Figure 10A:
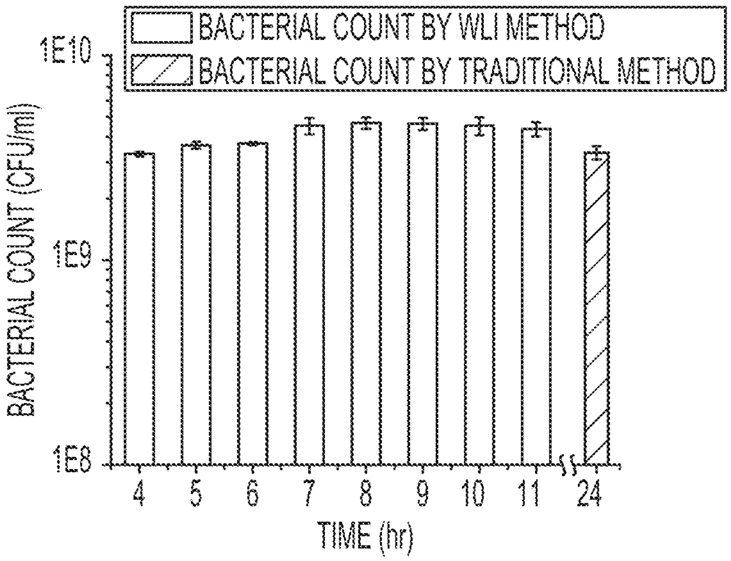
FIGS. 10A and 10B include graphs comparing bacterial counts in agar plate cultures using WLI and traditional methods (rightmost bar) for *Pseudomonas fluorescens* (10A) and *Bacillus thuringiensis* (10B). The WLI imaging method was used to count the colonies at several times including as early as 2 hrs after plating. The graphs show that the earliest measurement with the WLI method (leftmost bars) are accurate and have comparable error range to the traditional method (rightmost bars) in both cases. Error bars show standard deviation (n=4).
Figure 10B:
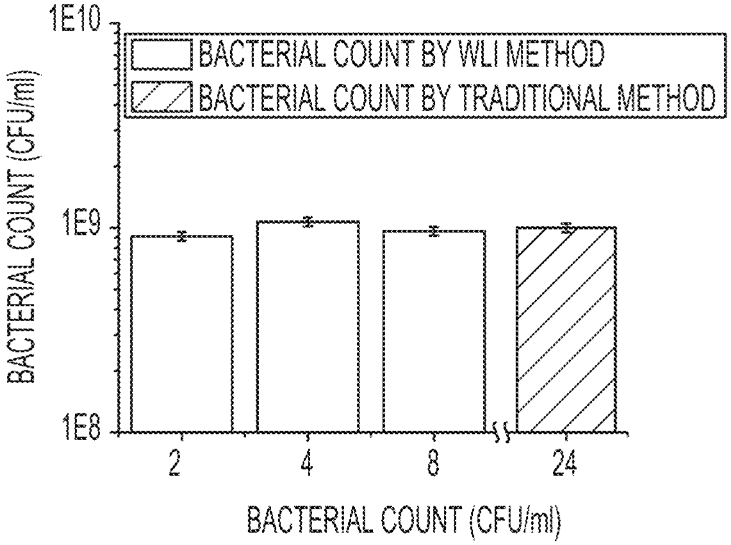

Analysis using the methods of this invention was able to detect most colonies and enumerate the CFUs in each culture, even at the earliest imaging times (4 hrs for PF and 2 hrs for BT). Subsequent experiments showed that both species could be detected and enumerated as early as 2 hrs after plating. Accurately detecting the microcolonies became easier with time as the colonies grew and their structures were more pronounced above the background. Filters can be applied to remove errant peaks, such as those caused by substrate imperfections, dust and other contaminants. Removing errant peaks becomes easier as the bacterial colonies become larger and more pronounced. As a result, the analysis algorithms get more accurate as colony size increases. FIG. 10 shows the enumeration of PA and BT from wide field WLI images. The number of microcolonies in the images was converted to CFU/ml to facilitate comparison with a standard CFU counting method. If the WLI counting method is accurate we would expect the CFU counts to remain consistent over time because while the bacteria are multiplying exponentially the number of colonies on the plate is not changing. FIG. 10A shows that there is a slightly non-linear trend in CFU counts of PF over time. The number of PF colonies detected increased steadily until about 8 hrs and then began to decline. It was clear during the analysis that in the first few hours after plating it was more difficult to distinguish bacteria from the background. Thus, a small fraction of some shallow colonies were not counted. With time the missing colonies grew taller and were easier to detect. It should be pointed out that this data is from colonies grown on agar that is not optimized for smoothness, which would reduce or eliminate this problem. The number of colonies declined after 8 hrs because some colonies grew large enough that they merged with nearby colonies and were undercounted as a result. Using measurements acquired according to embodiments described herein to enumerate CFU just hours after plating resulted in accurate colony counting as compared to traditional methods.

The final entry of both graphs shown in FIG. 10 is the CFU count in each culture made with a traditional method. The cultures used for WLI imaging were also spread over agar plates in dilution series. Then CFUs were counted by visual inspection after an average of 24 hrs incubation (i.e., 19 hours for BT and 29 hours for PF), approximately the time at which colonies could first be seen with the naked eye.

The CFU count of the PF culture at 8 hrs using the WLI method (4.67e9±2.9e8 CFU/ml) was not significantly different from the count made at 24 hrs (3.35e9±2.5e8 CFU/ml) using the traditional method. Likewise, the CFU count of the BT culture at 8 hrs using the WLI method (9.63e8±1.42e8 CFU/ml) was not significantly different from the count made at 24 hrs (1.00e9±1.29e8 CFU/ml) using the traditional method. The error ranges of the two methods are nearly the same. These results indicate that embodiments described herein can be used as a substitute method to enumerate CFU in plate culture with several advantages: CFU can be measured earlier than with traditional methods, as early as 2 hrs. The time required to count bacterial colonies using this invention is over 10× less than the time needed for traditional measurement methods of CFU counts from plate cultures. Additionally, the method of this invention uses fewer and smaller plates than would be required with traditional methods. Finally, because the method of this invention can distinguish and count a large number of colonies in a small area the culture may be plated with fewer time-consuming dilutions.

Figure 11A:
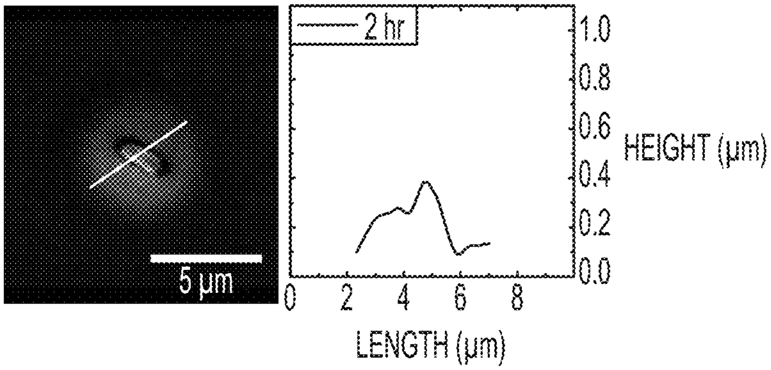
FIGS. 11A-11C include high magnification images and related line profiles acquired by WLI. Single cells can be resolved with 2 hours after plating (See 11A). The bacteria grow and divide as seen in 11B. Line profiles at right of each of 11A-11C distinctly show 1 protrusion at 2 hrs in 11A and 3 side-by-side protrusions at 6 hrs (11B). The profiles also reinforced the fact that the bacteria only extend a few hundred nanometers above the surface of the agar. Just 30 minutes after the image shown in 11B, the morphology of the microcolony changes and becomes smoother, a possible indication of EPS formation (11C). Lateral scale as shown by the bar in each image. Vertical scale is represented by grayscale false color with a 0-1 μm vertical range.
Figure 11B:
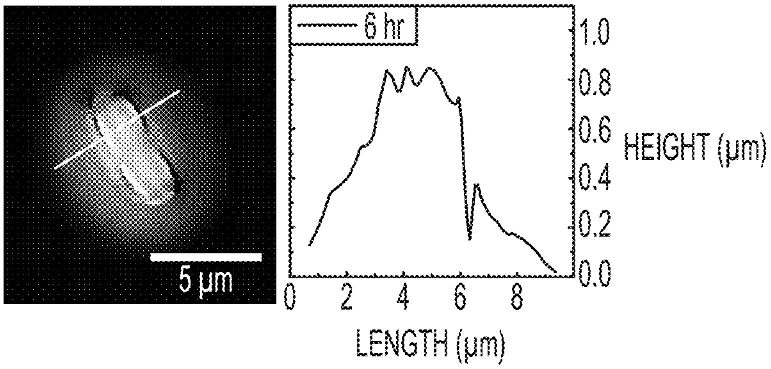
Figure 11C:
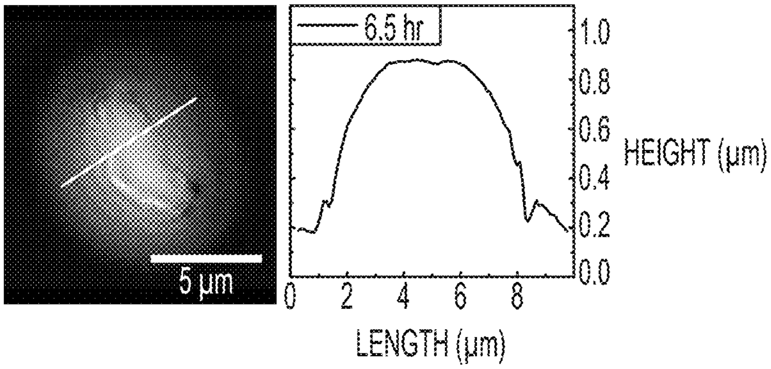

As shown in FIG. 10, embodiments described herein were used to observe morphology and growth of bacterial colonies and enabled accurate measurements of total microbial population (volume) and growth rates of individual colonies. The images were further analyzed to identify morphological changes associated with phenotypic changes. FIG. 11 shows three images of a PF culture range from single cell to mature colony. The initial image, FIG. 11A, clearly shows a single microbe. Over time the cell divides and each new cell is visible, though somewhat less clearly. Extracting line profiles over the colony (shown to the right of each image) assists in delineating individual bacteria. However, between 6 hrs and 6.5 hrs the surface morphology of the colony changes dramatically. The undulations of individual bacteria transformed into a more uniform mass. This morphological change is indicative of a transition to a biofilm state. Biofilms exhibit unique features from individual/planktonic bacteria (of the same species), including the excretion of extracellular substances that create a smooth protective layer over the colony. The biofilm state of bacteria is an important factor in several diseases, including cystic fibrosis. Detecting the timing of the morphological change to a biofilm state is difficult. Using the methods disclosed herein the dramatic change was observed to occur over a period of 30 minutes. The same methods with more frequent imaging could be used to further study the phenomenon and the environmental factors that impact formation and development of biofilms. Doing so would allow us to better understand the biological factors that trigger a transition to a biofilm state and would help to understand diseases such as cystic fibrosis.

Figure 12A:
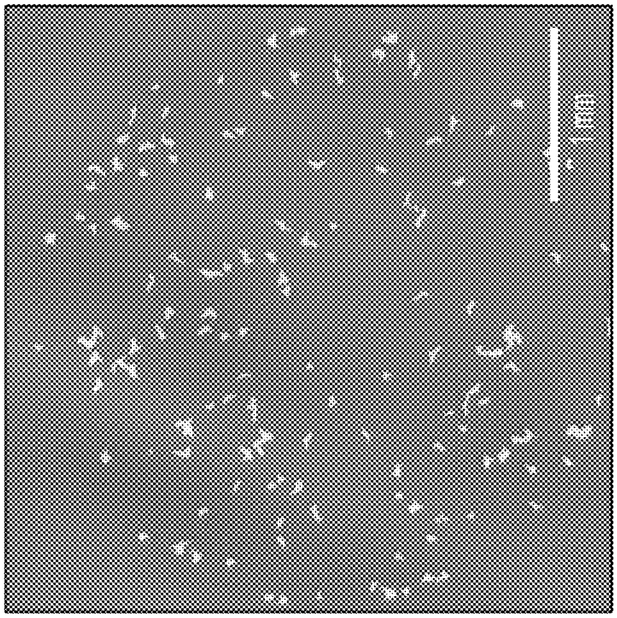
FIGS. 12A-12E are images showing WLI surface profiles of agar plates with (12A) *Bacillus thuringiensis*, (12B) *Pseudomonas fluorescens* and (12D) a roughly 50/50 mixture of both. The two species in the mixed culture shown in 12D were identified by morphological traits and separated into two separate images by threshold filtering. (12C) The *Bacillus thuringiensis* portion of the culture and (12E) shows the *Pseudomonas fluorescens* portion. Lateral scale as shown by the bar in each image. Vertical scale is represented by grayscale false color with a −1.8 to 1.8 μm vertical range for 12A and 12D. 12B has a −150 to 150 nm vertical range. 12C is shaded via threshold for objects taller than 1 μm and E is colored via threshold between 80 and 180 nm.
Figure 12B:
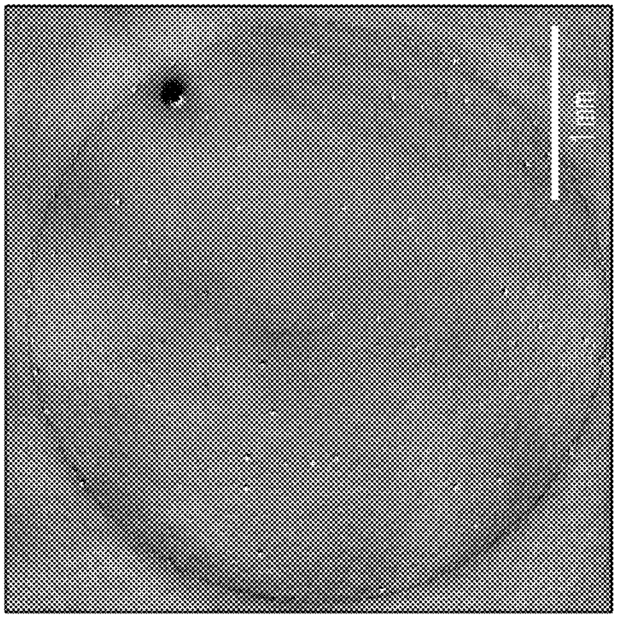
Figure 12C:
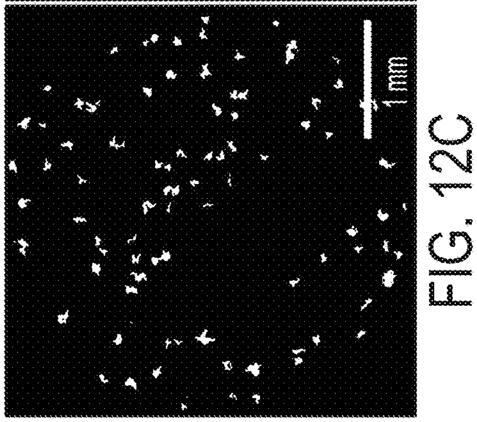
Figure 12D:
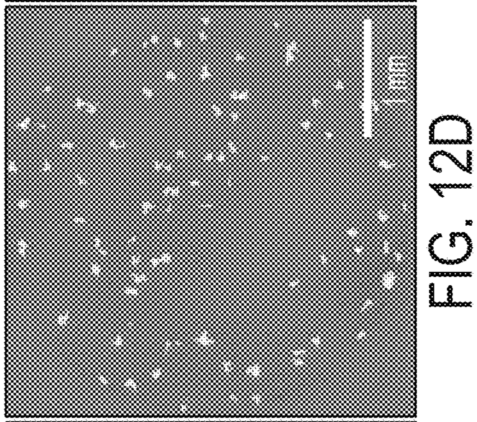
Figure 12E:
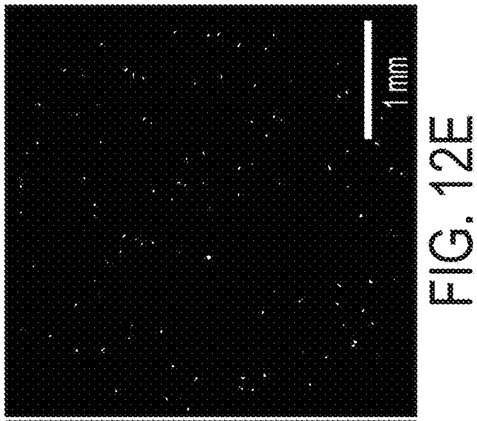

The results above show that embodiments described herein have many capabilities to study monoculture samples of individual microcolonies or many colonies in parallel. Biofilms and clinical and environmental samples are almost always mixed cultures with many species. An experiment was conducted to determine if the embodiments could be used to differentiate or identify species in a mixed culture. Three plates were prepared with cultures of BT (FIG. 12A), PF (FIG. 12B), and a mixture of both (FIG. 12D). Images were collected 2, 4, and 8 hrs after plating. The composition of the culture on each plate was easily identified at 2 hrs despite being unknown prior to imaging because WLI imaging clearly showed distinguishing morphological features. FIG. 12 shows images of the plates at the 8 hr mark. There are clearly morphological differences between BT (FIG. 12A) and PF (FIG. 12B). The BT colonies are larger (laterally), shorter, and have irregular shapes with large aspect ratios (length/width or perimeter/area). The PF colonies are smaller (laterally), taller, and are uniformly rounded. It is straightforward to separate the BT and PF portions of the mixed culture by filtering morphological traits measured with embodiments described herein (microcolony height, microcolony shape, morphology, and volume). The images shown in FIGS. 12C and 12E are filtered versions of the image shown in FIG. 12D that highlight the ability to separate and classify BT (12C) and PF (12E) when they are grown together in the same culture.

Figure 13A:
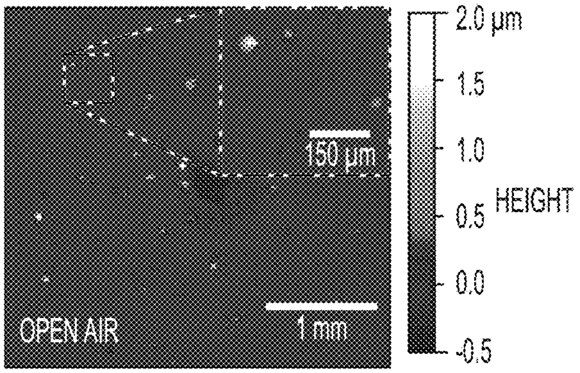
FIGS. 13A-13D include images comparing WLI surface profile images of a *Pseudomonas fluorescens* agar sample captured (13A) in open air and then in a system enclosed with a plate cover (13B). Inset images in 13A and 13B show of the same fine morphological details can be resolved in air and in an enclosed plate. Comparison of smooth region of agar as imaged through open air (13C) and through the glass lid of a sealed plate (13D). Lateral scale as shown by the bar in each image. Vertical scale is represented by false shading as shown at right.
Figure 13B:
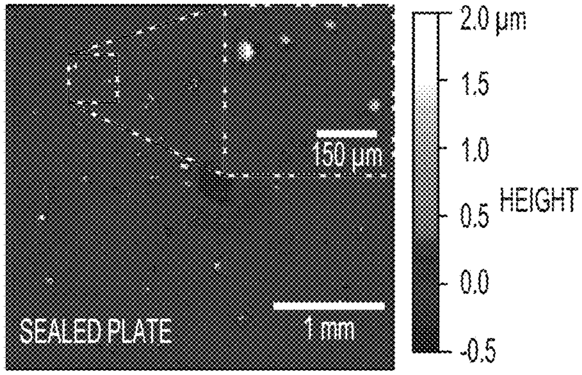
Figure 13C:
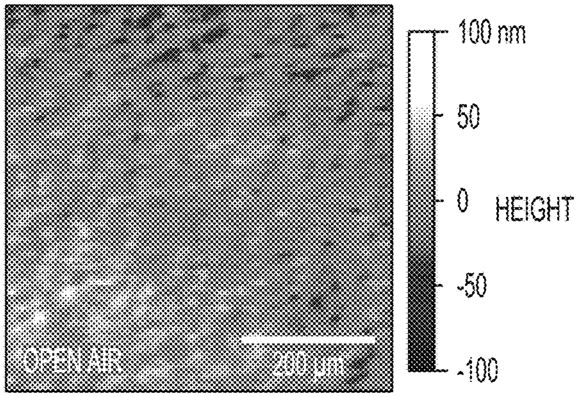
Figure 13D:
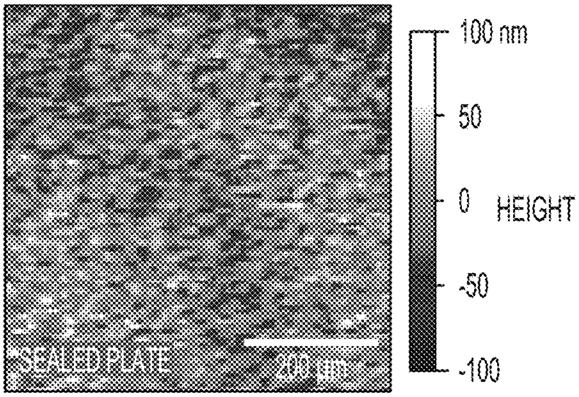

Another capability of WLI is that one can image a sample through transparent materials. An experiment was conducted to determine if it was possible to enumerate bacterial colonies on an agar plate that was sealed in an environmentally controlled and sealed system with a transparent lid to enable measurement. Imaging closed plate cultures would reduce the risk of contamination, especially for slow growing bacteria and would also facilitate growth in controlled environments. FIG. 13 shows a comparison of a plate culture imaged in open air (13A and 13C) and the same culture imaged in a sealed plate (13B and 13D). There are some modest differences in the two images (as seen in the magnified inset images) from the prototype system that do not impact the ability to accurately count CFUs in the culture. Improvements in window materials and imaging algorithms to future systems could eliminate most of the artifacts resulting from imaging through a window. The number of colonies (averaged from 3 equally prepared plates) were statistically the same; 50±3.6 for the open plate and 51.7±5.8 for the sealed plate. FIGS. 13C and 13D show a smooth region of the agar plate with no microcolonies. There appears to be a slightly higher level of noise in the image obtained through the lid of the sealed plate. A moderate increase in root-mean-squared roughness ($S_q$) from 18.3 nm to 28.9 nm resulted from imaging through the glass lid, though the change had no apparent effect on the ability to accurately count and characterize bacterial colonies. The plate cover was modified with a thin coverglass window to ensure a minimal change to the optical path length to the sample. This demonstration of CFU enumeration in a sealed plate shows that WLI could be integrated into existing standard procedures without introducing risks of contamination of other samples as well as providing a control environment for sample growth. The ability to ascertain CFU counts shortly after plating also means that data can be collected before a fast-growing contaminant overtakes colonies of interest.

As mentioned above most experiments were performed with open agar plates. Exposure to dry laboratory air often resulted in the agar shrinking over time. This was evident because colonies of interest continuously lowered from their original position and slowly shifted laterally as well as a result of desiccation and shrinking of the nutrient agar medium. These shifts were especially apparent when imaging the sample at high resolution. These shifts made it difficult to maintain the culture in focus. A method for imaging with a closed plate was developed in part to mitigate this problem. However, if the sample was closed the interior of the lid was prone to accumulate condensation that inhibited imaging. Moreover, a standard polycarbonate plate lid could not be used without optical compensation in the reference arm of the interferometer. In some embodiments, an optically-compatible lid was used for closed plate imaging. In other embodiments, a multi-well plate (e.g., a 96-well plate) with each well filled with agar can be used to create an array of microplates because the diameter of a single well in a standard microtiter plate is similar to the diameter of culture spots observed in this study. This would also enable controlled parallel experiments on a single platform.

An important consideration when imaging microbial colonies in a closed plate systems is the selection of the viewing window. Glass coverslips are typically placed over objects for viewing with an optical microscope where their main function is to keep the sample flat and to prevent contact between the immersion liquid (typically oil or water) and the sample. Coverslips are not typically used with WLI imaging because there is no immersion liquid and because the smooth glass would obscure texture of the underlying sample. For microbial colony imaging with WLI, a coverslip may be placed in the space between the sample surface and the objective lens and serve to maintain environmental conditions (humidity, temperature, etc.) that support microbial growth. As with any interferometric imaging through transmissive media it is important that the coverglass is transparent and smooth. Thickness of coverslip glass is a limiting factor when imaging microbial colonies. Light transmitted through the higher index coverslip glass traverses a longer optical path length than it would through air. The increase in optical path length from the coverslip cannot exceed the depth of field of the objective (as shown in Table 1). If the shift in optical path length is greater than the depth of field enabled by the objective lens then the image will not appear in focus at the length fixed in the reference arm of the interferometer. However, calculations shown below reveal conditions in which transmitting light through a thin coverglass over the sample will not prevent light interference.

Using Equation 1 the depth of field ($d_{tot}$) for an interferometric objective can be calculated. For this example, a lens with 2.5× magnification (M) with numerical aperture (NA) of 0.07 was used. This lens is suitable for imaging large areas (~5 mm) microbial cultures grown on nutrient agar plates. Middle wavelength ($\lambda_o$) of illuminating light was approximately 550 nm (from a green light-emitting diode). The smallest lateral resolving distance (e) is 3.8 μm and the refractive index (n) of the immersion media (air) is 1. Given these parameters the depth of field is approximately 133 μm, which is on the order of the thickness of a typical cover glass. Since the angle of incidence is small the optical path length through glass can be approximated as the thickness multiplied by the refractive index (OPL=T·M) and the increase in optical path length is simply the difference between the thickness and the optical path length (OPL−T). Table 1 shows the thicknesses of various glass coverslips and the corresponding increase in optical path length caused by imaging through the glass.

Coverslips up to approximately 250 μm are suitable for transmission imaging with a low magnification lens because the increase in optical path length does not exceed the depth of field. Table 2 illustrates the decline in depth of field at higher magnification. The narrow depth of field for high magnification lenses limits ability to image through glass viewing windows. Even at magnification as low as 5× the depth of field is prohibitively narrow. With higher magnification it would be necessary to compensate for the increase in optical path length by inserting a sample of equal thickness in the reference arm of the interferometer. In any case, the spatial resolution of the low magnification lens is sufficient to observe microcolony morphology and the large field of view is actually an advantage over other imaging modalities. For experiments described here No. 2 coverslips were used.

$$d_{tot} = \frac{\lambda_o n}{NA^2} + \frac{n}{M \cdot NA} e \qquad (1)$$

TABLE 1

The increase in optical path length of several coverslips of varying thickness

| Coverslip | Thickness (μm) | Optical path length increase (μm)* |
|---|---|---|
| No. 0 | 85-130 | 42.5-65 |
| No. 1 | 130-160 | 65-80 |
| No. 1.5 | 160-190 | 80-95 |
| No. 2 | 190-230 | 95-115 |
| No. 3 | 250-350 | 125-175 |

*Calculated as the difference between optical path length and thickness

TABLE 2

Depth of field for lenses of different magnification.

| Magnification | Depth of field (μm)* |
|---|---|
| 2.5 | 133 |
| 5 | 42 |
| 10 | 6.4 |
| 20 | 3.5 |
| 50 | 1.8 |

*Calculated using Equation 1.

Treating bacteria with a below lethal dose of antibiotics is a significant risk factor in the development of anti-bacterial resistance. Bacteria that are exposed to antibiotics and survive can become resistant. It is therefore valuable to be able to detect and quantify sub-lethal effects of antibiotics. Traditional plate counting methods cannot achieve this because for many sub-lethal conditions do not affect the number of colony forming units. Sub-lethal conditions may, however, affect growth rate of microbes, which can be measured and quantified using the methods and apparatuses described herein.

A test was conducted to demonstrate the ability to measure effects of antibiotics with the methods described herein. A common antibiotic (kanamycin sulfate) solution (Thermo Fisher Scientific, 15160054) was mixed into LB agar so the resulting concentration ranged from 2 μg/ml to 40 μg/ml. Agar without antibiotics additives was used as a control. The agars were poured into petri dishes and allowed to cool. As described above, a culture of PF was prepared and pipetted onto the surface of the agar. The plates were incubated for 8 hrs and then imaged with the interferometric microscope every 2-3 hours until 21 hrs had elapsed. Images from the 16 hr mark showed clear bacterial colonies and were further analyzed to count and characterize the microcolonies growing with each concentration of antibiotics.

Figure 14:
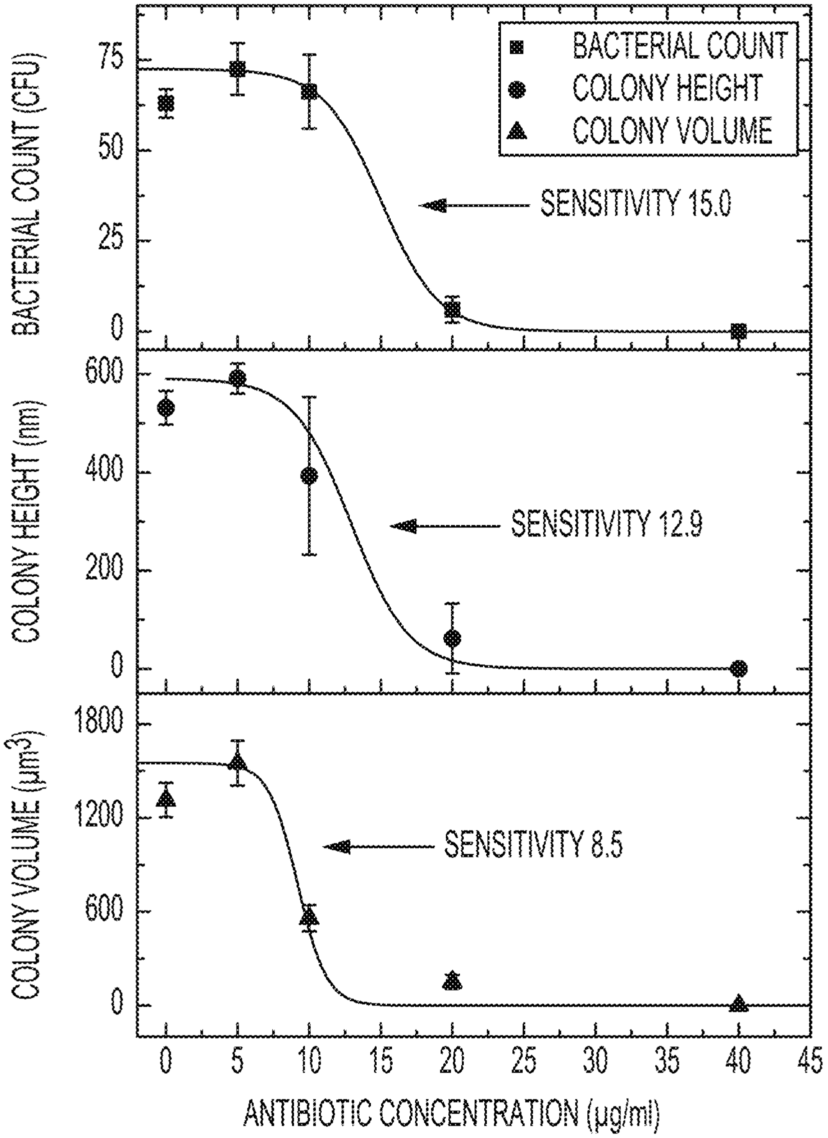
FIG. 14 is a plot showing the effect of antibiotic concentration (μg/ml) on the number of colonies or bacterial count (top), the average height of colonies (middle), and the average volume of colonies (bottom). The inflection points of the antibiotic response curves indicate the sensitivity of each method for observing antibiotic effects—i.e., the lowest antibiotic concentration which impacts bacterial growth. The methods of this invention are the most sensitive. All data are averages from n=4 samples. Error bars show standard deviation.
Figure 15A:
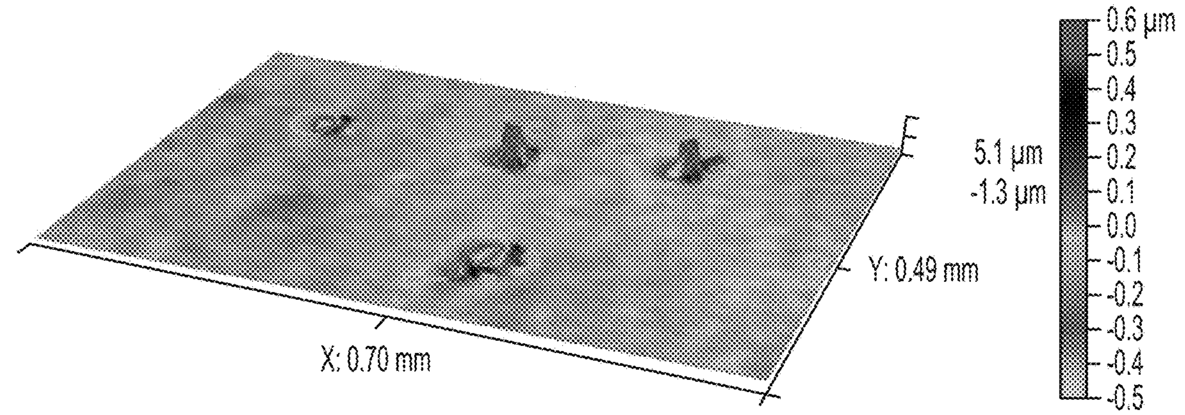
FIGS. 15A and 15B are two 3D images showing representative sample portions of two agar plates with cultures of PF. The images show colonies of PF bacteria growing (15A) in a control condition without any antibiotic treatment and (15B) in an agar plate with a non-lethal dose (10 μg/ml) of the antibiotic Kanamycin sulfate. Colonies are noticeably and measurably smaller (15B) compared to the control despite there being no statistically significant difference in the number of colonies in each of the plates (including an area larger than the field of view shown). The methods described herein are able to detect when an antibiotic treatment is partially effective, which is an undesirable condition that can lead to antibiotic resistance.
Figure 15B:
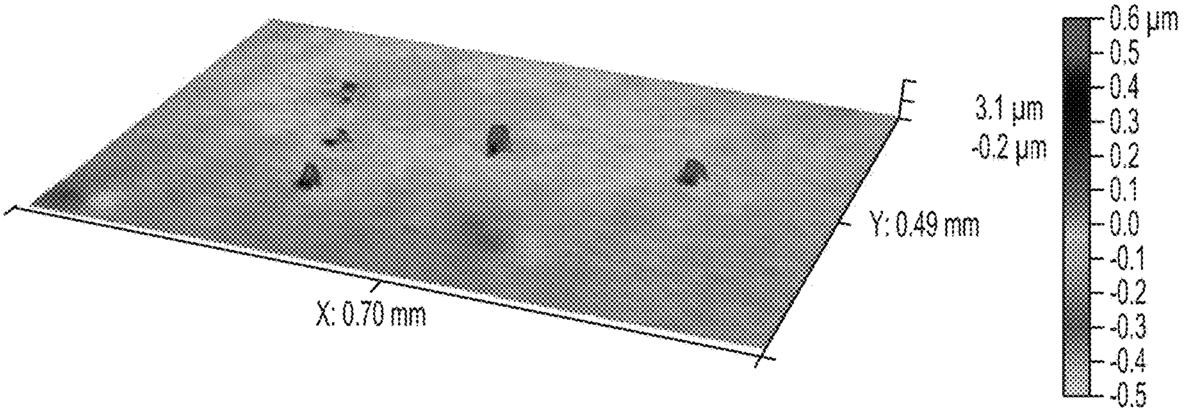

FIG. 14 shows the effects of the antibiotic solutions on PF bacterial growth. The figure shows the count of bacterial colony forming units, the average height of colonies over the surround agar, and the average volume of the colonies. Each plot is fitted with a Boltzmann curve. The traditional colony counting method showed no effect of antibiotics until the concentration reaches 20 μg/ml. The inflection point of the fitting curve is 15.0 μg/ml, which is a good indicator of the method's sensitivity. The second method of quantification—measuring the average height of colonies—showed a small but noticeable decline when the antibiotic concentration was 10 μg/ml and the inflection point for the fitted curve was 12.9, modestly more sensitive than the colony counting method. FIGS. 15B and 15A show representative sample portions of plate cultures of PF grown on media with and without antibiotics, respectively. The plate with antibiotics (FIG. 15B) had a sub-lethal concentration of kanamycin sulfate (10 μg/ml). The figure clearly shows that colonies grown on plates containing antibiotics were smaller in both height and volume, despite there being no significant difference in the number of colonies on each plate (not all colonies on the plates are seen in the images). Measuring the volume of colonies grown on plates with varying concentrations of antibiotics that a significant difference in volume can be observed at concentration 10 μg/ml. The inflection point of the Boltzmann fit curve was 8.5, indicating a sensitivity that is significantly better than the traditional method. At low concentration (0 and 5 μg/ml) there was no statistically significant effect that is observed using any of the three methods. These results indicated that high resolution measurement of microcolony volume is a viable way to measure sub-lethal effects of antibiotics or other treatments.

This example illustrates unique and valuable information that can be observed and quantified using the methods described herein. It is reasonable that those skilled in the practice could conduct similar tests with a wide variety of antibiotics and other anti-microbial treatments. In addition, because the methods described herein do not require large sample volumes many tests can be conducted in parallel. For example, testing a selection of antibiotics (each with a range of concentrations) in parallel would confer significant benefits. A practitioner could determine which antibiotics are effective against a given bacteria and which concentrations are effective. This would inform treatment strategies. Results of such a test would be available quickly, as detailed above.

Figure 16:
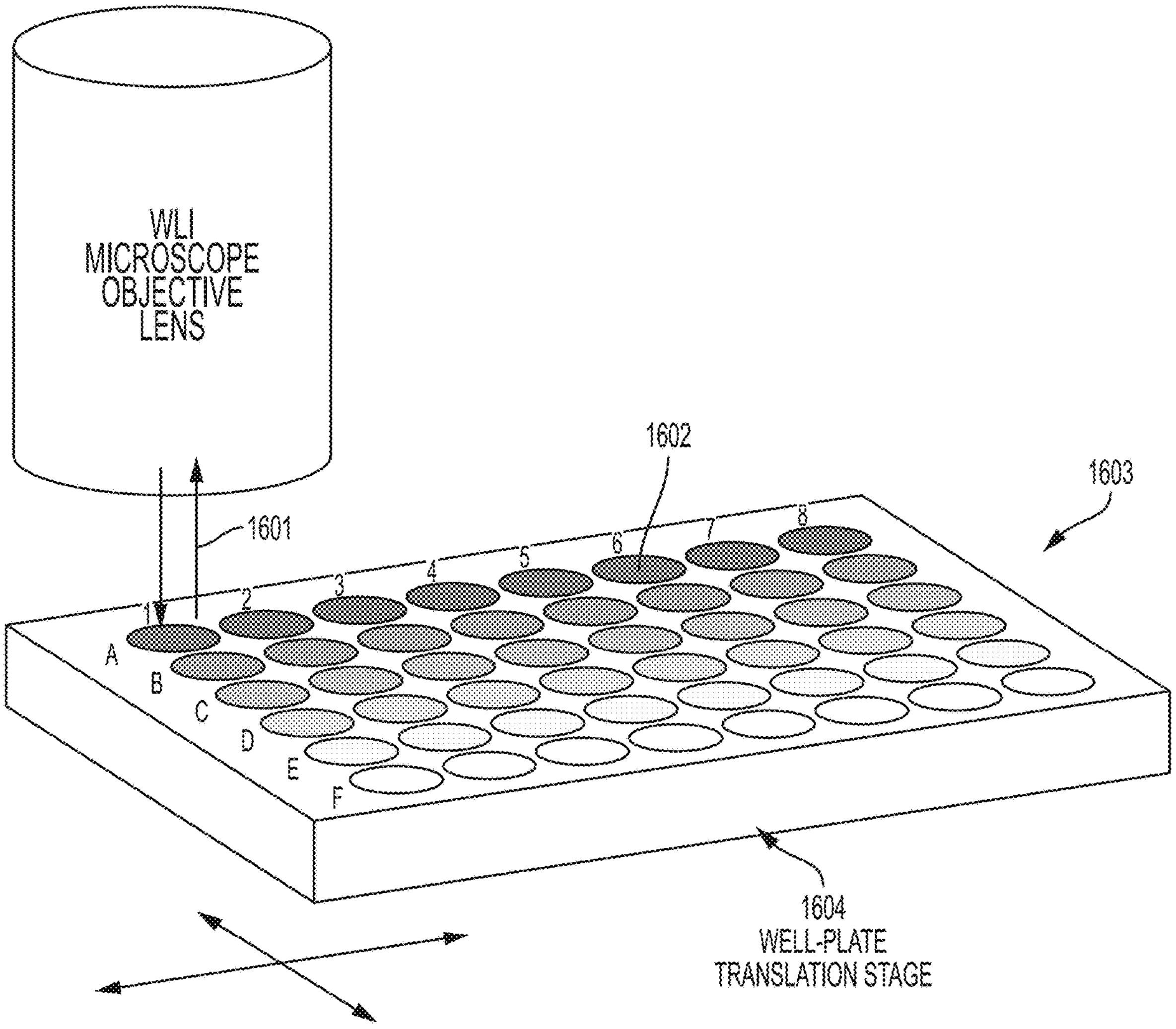
FIG. 16 is an illustration showing an embodiment of multiple small area culture plates arranged in a grid. Each culture area may have a different type and concentration of antibiotic. Imaging each well with the described methods may proceed in a mechanized and automated manner.

FIG. 16 shows one embodiment of how to conduct combinatorial biological testing, specifically how a parallelized test of antibiotic susceptibility could be carried out using a multi-well plate. Alternative testing can include non-antibiotic compounds. Examples can include but are not limited to toxins, chemicals, materials, and surfaces. Surfaces can be used to test antimicrobial properties and/or biofouling resistance. The figure shows one embodiment of a rectangular plate 1603 with 48 equal size wells 1602 arranged in a grid. The wells can each be filled with a growth medium having a smooth culture surface. A translation stage, which can be motorized and/or computer-controlled, can position each well in appropriate alignment with a probe from the vertical scanning interferometer 1601. Multi-well plates are not typically filled with semi-solid agar; however, doing so would confer specific benefits for the methods described herein. For example, each column of wells (labeled 1-8) could have a different antibiotic or anti-microbial treatment mixed into the agar. Each column (labeled A-F) could have different concentrations of the selected antibiotics. Pipetting replicate samples onto each of the wells in the plate, incubating, and then imaging each of the wells with the methods described herein in order to count and quantify bacterial growth in each condition would result in a rapid assessment of antibiotic susceptibility. WLI imaging is easily automated and can be optimized for high throughput. Embodiments of this invention may include automation of the imaging process including automatic movement from one sample to another in a multi-sample grid. Automation may further include the preparation of samples, the movement of samples into position for imaging, and disposition of samples.

As indicated in the above examples using the methods described herein it is possible to count colony forming units in a microbial culture using a relatively small area of nutrient growth media or agar. For example, the diameter of a typical petri plate used for CFU counting is 100 mm. The above examples have demonstrated that the same result can be achieved using a plate area that has a diameter of only 5 mm. In fact, multiple small area plates can be combined into a standard format, as is done in multi-well plates. In one embodiment 96 small area plate cultures could be conducted on a plate measuring 85 mm by 125 mm, approximately the same area as a single large area plate. This would have several benefits. First, less material would be used to conduct a test. Second, less space would be needed to incubate, process, and store bacteria culture plates. Incubation space, in particular, is costly because bacterial cultures often require tightly-controlled elevated temperatures, which may use a significant amount of energy. Reduced incubation times further reduces dependence on this costly resource.

As illustrated through the above examples and comparative test data the methods and principles of this invention confer specific and measurable benefits to rapid identification and quantification of microbial cells and cultures. There are many applications for these methods that would benefit from faster and/or more accurate information. One such area is in food safety testing. In cases of microbial food contamination it is desirable to identify the source of contamination as soon as possible, before food is distributed for consumption, if possible. Embodiments of this invention would enable microbial testing results in just a few hours, significantly less than the 1-3 days for results by current state-of-the-art methods. Similarly, in clinical and biomedical settings there is a need to rapidly diagnose bacterial infection, especially sepsis. In some cases the repercussions of a sepsis infection are so severe that medical professionals prefer to treat patients as if they had an infection, even if it has not been confirmed. The disclosed invention would enable rapid detection of microbial infection and lead to more suitable and timely clinical treatments. Even in cases much less severe than sepsis, such as an upper respiratory infection, it is often difficult to discern whether an infection is caused by bacteria, which can be treated with antibiotics, or by a virus, which cannot. The disclosed invention would be able to detect if the causative agent of an infection grows in colony forming units (bacteria) or does not (virus). The ability to make that determination in just a few hours would enable timely delivery of appropriate treatments. Likewise, it would also be possible to detect susceptibility to specific antibiotic treatments and the dosing of those treatments that is necessary to quell an infection In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. A method comprising:

non-destructively acquiring by a vertical scanning interferometer a three-dimensional (3D) profile that provides a height measurement of a microcolony on a surface, the microcolony comprising a microbial colony forming unit (CFU);

computing a sample parameter based on the 3D profile with the height measurement; and enumerating, identifying, and differentiating a species among a plurality of species of the microbial CFU based on the sample parameter.

2. The method of claim 1, wherein the surface comprises that of a solid growth medium.

3. The method of claim 1, wherein a vertical resolution of the vertical scanning interferometer is less than or equal to 5 nm.

4. The method of claim 3, wherein said acquiring comprises laterally sampling an area of the growth medium that is greater than or equal to 10 mm, 8 mm, 5 mm, 3 mm, 1 mm, 0.5 mm or 0.05 mm across.

5. The method of claim 1, wherein the vertical scanning interferometer is a white light interferometer.

6. The method of claim 1, wherein the sample parameter comprises a value based on microcolony height, aspect ratio, volume, number of microcolonies, microcolony morphology, or a combination thereof.

7. The method of claim 1, further comprising estimating a microbial CFU population value based on the sample parameter.

8. The method of claim 1, wherein said computing occurs at a non-zero time value that is less than 1 hour, 2 hours, 4 hours, 6 hours, or 8 hours after the microbial CFU is introduced to a solid growth medium.

9. The method of claim 8, further comprising estimating a growth rate value of the microbial CFU based on the sample parameter and on changes over the period of time.

10. The method of claim 1, further comprising tracking changes in the sample parameter over a period of time.

11. The method of claim 1, further comprising screening a plurality of samples by repeating said acquiring and said computing at each of a plurality of sample wells, each sample well comprising a solid growth medium.

12. The method of claim 11, wherein the plurality of sample wells have different solid growth media selected from the group comprising culture media, minimal media, selective media, differential media, transport media, and combinations thereof.

13. The method of claim 11, wherein the plurality of samples wells each have a non-zero dimension that is less than or equal to 50 mm, 30 mm, 15 mm, 10 mm, or 5 mm.

14. The method of claim 1, further comprising covering the surface of a solid growth medium with a lid comprising an optically transparent window through which light of the vertical scanning interferometer passes.

15. The method of claim 1, wherein the surface of a solid growth medium has a non-zero root mean squared roughness value less than or equal to 200 nm, 125 nm, 100 nm, or 50 nm.

16. A non-transitory computer readable storage medium storing one or more programs, the one or more programs comprising instructions, which when executed by one or more processors of an electronic device comprising, or operably connected to, a vertical scanning interferometer, cause the device:

to acquire a 3D profile with a height measurement of a microcolony grown on a surface, the microcolony comprising a microbial colony forming unit (CFU); and to compute a sample parameter based on the 3D profile with the height measurement, enumerate, identify, and differentiate a species among a plurality of species of the microbial CFU based on the sample parameter, and determine a microbial CFU population value in a microcolony.

17. The non-transitory computer readable storage medium of claim 16, wherein the sample parameter is one of microcolony height, aspect ratio, volume, number of microcolonies, microcolony morphology, microcolony count, or a combination thereof.

18. The non-transitory computer readable storage medium of claim 16, which when executed by one or more processors of an electronic device comprising, or operably connected to, a vertical scanning interferometer, further cause the device to estimate a growth rate value of the microbial CFU, provide a positive/negative outcome of a diagnostic test, indicate a biofilm state, or perform a combination thereof based on one or more of the sample parameters.

* * * * *